(12) United States Patent
Mizuoka et al.

(10) Patent No.: US 6,872,949 B2
(45) Date of Patent: Mar. 29, 2005

(54) CONNECTION INSPECTING APPARATUS, CONNECTION INSPECTING METHOD, AND RECORDING MEDIUM FOR RECORDING PROGRAMS EXECUTING THE METHOD

(75) Inventors: Seiji Mizuoka, Yamanashi-ken (JP); Masaru Ichihara, Osaka-fu (JP); Noriyuki Suzuki, Osaka-fu (JP); Haruko Kubota, Osaka-fu (JP); Kazumasa Okumura, Kyoto-fu (JP)

(73) Assignee: Matsushita Electric Industrial Co., Ltd., Osaka-Fu (JP)

( * ) Notice: Subject to any disclaimer, the term of this patent is extended or adjusted under 35 U.S.C. 154(b) by 179 days.

(21) Appl. No.: 09/816,155

(22) Filed: Mar. 26, 2001

(65) Prior Publication Data

US 2001/0040217 A1 Nov. 15, 2001

(30) Foreign Application Priority Data

Mar. 28, 2000 (JP) .................................. 2000-088801

(51) Int. Cl.$^7$ ............................................. G01N 23/04
(52) U.S. Cl. ............................ 250/358.1; 250/361 R; 378/54; 378/56; 324/501
(58) Field of Search ..................... 250/358.1, 361 R; 378/54, 56; 324/501

(56) References Cited

U.S. PATENT DOCUMENTS 4,926,452 A * 5/1990 Baker et al. ................... 378/22
5,836,504 A * 11/1998 Koike et al. ................. 228/103
6,201,850 B1 * 3/2001 Heumann ..................... 378/56
6,256,406 B1 * 7/2001 Garland et al. ............. 382/132

* cited by examiner

Primary Examiner—Constantine Hannaher
Assistant Examiner—Shun Lee
(74) Attorney, Agent, or Firm—Wenderoth, Lind & Ponack, L.L.P.

(57) ABSTRACT

Brightness information of, for example, an average value of brightnesses at an X-ray image of a first connected part when an electronic component is mounted onto only one face of a printed board is obtained. Binary images of an X-ray image of the board with the electronic components mounted to both faces are formed by an upper and a lower levels relative to the brightness information. The binary images are synthesized with each other so as to extract an image of only a second connected part. The image of only the second connected part can be obtained in this manner on the basis of the X-ray image of the double face-mounted board, so that an accuracy for connection inspection is improved. Also, a relationship between a density in the X-ray image of the connected part and a thickness of the connected part is obtained beforehand, based on which a plurality of thickness images are obtained for a plurality of X-ray images of different image storage times. The connected part can be inspected by synthesizing the images.

30 Claims, 18 Drawing Sheets

BINARIZED IMAGE OF LEFT SIDE OF DIVIDE LINE

BINARIZED IMAGE OF RIGHT SIDE OF DIVIDE LINE

BINARIZED IMAGE OF ONLY CONNECTED PART OF B FACE

CONNECTION INSPECTING APPARATUS, CONNECTION INSPECTING METHOD, AND RECORDING MEDIUM FOR RECORDING PROGRAMS EXECUTING THE METHOD

FIELD OF THE INVENTION

The present invention relates to an apparatus and a method for inspecting with X-ray images connection states by brazing between electrodes of a surface mounted component including an electronic component with the electrodes set to a rear face such as flip chips, BGAs (ball grid array), CSPs (chip scale package), etc., and electrodes of a circuit board, e.g., in a field of mounting electronic components; and a recording medium for recording programs executing the connection inspecting method.

BACKGROUND OF THE INVENTION

In these days, products in a market of electronic devices such as portable information devices and the like have been required to be compact and light-weight, which correspondingly increases the demand for forming circuit boards constituting the electronic devices to be compact and light-weight as well. Under these circumstances, package products such as BGAs reduced in package size by setting electrodes to rear faces of electronic components, CSPs of a nearly equal size to a semiconductor bare chip by further miniaturizing the BGA, and the like, and moreover, flip chip mounting for directly mounting onto a circuit board via bump electrodes of a semiconductor bare chip without forming a package are starting to be widely adopted.

However, the above flip chip electronic components such as BGAs, CSPs or the like have electrode connection parts set to the underside which cannot be seen from outside, thus hindering visual inspection to the connected parts, unlike conventional electronic components with leads. Nondestructive inspection using X-rays or the like should therefore be realized.

There is a method for inspecting whether or not electrodes of an electronic component and of a circuit board having the component already mounted are connected well with the use of a conventional transmission type X-ray inspecting machine to meet the above demand, in which X-rays passing the circuit board and the electronic component on the circuit board were converted to an image by an X-ray generator arranged to apply X-rays perpendicularly to the circuit board with the component mounted and by an X-ray detector for detecting the X-rays passing the circuit board, whereby the image was visually inspected or automatically inspected by an image recognition device. A positional deviation of a connected part, a short circuit of electrodes, excess/deficiency and voids of a connecting material such as solder or the like, scattering of solder balls, contamination by a foreign substance, etc. have been inspected in this manner.

In general, heavy metal materials such as lead, tin or the like of a high index of absorption to the X-rays are used as the connecting material for the electronic component and circuit board. The picked connecting material in the X-ray image is black, and therefore can be distinguished from a surrounding part of the connecting material. Since it is necessary to obtain a thickness of the connecting material such as solder or the like in three dimensions particularly for inspecting excess/deficiency of the connecting material, and since a quantity of the X-rays passing a substance decreases like an exponential function with respect to a thickness of the substance, a device or technique to obtain a relationship of the thickness of the object to be inspected and a density of the X-ray image has been needed.

In the related art, however, there is a problem that the X-ray image of a thin object exceeds a dynamic range of an image density and is saturated when a storage time for the X-ray is secured long enough to meet a thick object, as is clear from FIG. 12, due to the characteristic that the quantity of X-rays passing the substance decreases exponentially to the thickness of the substance and due to limits on the dynamic range of the image density and on a resolution of a pickup system. On the contrary, when the storage time for X-rays is secured short enough to match the thin object, there is a problem that the X-ray image of the thick object becomes a minimum density signal or smaller and cannot be measured.

When a double face-mounted circuit board is to be inspected by the above transmission type X-ray apparatus, components of a front face and a rear face of the circuit board are picked up overlapping, and hence hard to inspect by the ordinary pickup method and recognition method heretofore.

There is another method using X-rays for inspecting the double face-mounted board with components mounted to both faces of the board, whereby an X-ray generator disposed to apply X-rays slantwise to the circuit board with the components mounted, and an X-ray detector for detecting X-rays passing the circuit board are synchronously rotated on a plane parallel to the board, thereby obtaining a horizontal sectional image of the board with adjusting a focal point to a fixed height of the board while blurring the other faces in heights different from the fixed height by the rotary motion. Furthermore, an X-ray inspection method using a technique called X-ray laminography whereby the front side and rear side of the double face-mounted board can be inspected separately is actually put in use. However, the method is complicated in mechanism and thus expensive, with problems yet to be solved in terms of cost for the method to be practiced in mass production factories, although it can be executed at a laboratory level.

To solve the problems, an X-ray inspection method using an image differential which is simple in structure is being examined as a method for inspecting the double face-mounted board. According to the method, as shown in FIGS. 27 and 28, an X-ray image in a state with a component mounted only on one face (A face) is stored beforehand. After a component is mounted to a rear side (B face) of the board, the stored X-ray image of the one face (A face)-mounted board is subtracted from an X-ray image of the board of a state with the components mounted to both faces, so that an image of only the rear face (B face) is obtained.

The technique using the image differential as above necessitates not only storing the X-ray image of a large capacity of the one face-mounted board, but making sure that the one face-mounted board is identical to the board after the double-sided mounting, that is, requires holding images of the boards in a perfect one-to-one correspondence.

Even when images of the same board are matched in a one-to-one relationship, the board deflects during soldering with the use of a reflow or the like, bringing about a deviation between images. A perfect image of, e.g., only the rear face is not always obtained in spite of the subtraction to the transmission images, and noises are included. In other words, a positional deviation is generated between the X-ray image of the double face-mounted board and the X-ray image of the one face-mounted board. The positional deviation remains as noises hinder a correct judgment on the inspection. The X-ray inspection method using the image differential has not reached a practical level.

The present invention is devised to solve the aforementioned problems, and has for its object to provide an apparatus and a method for inspecting connection whereby an inspection accuracy for connected parts of mounted components can be improved in comparison with the related art, and a recording medium for recording programs executing the connection inspecting method.

SUMMARY OF THE INVENTION

In accomplishing the above-described objective and other features, the present invention provides a connection inspecting apparatus according to a first aspect, which comprises:

an irradiation part for applying radiation to the connected part of members with an application condition kept invariant;

a scintillator for converting the radiation passed through the connected part to visible light;

an imaging device for picking up transmission images of the connected part generated from the scintillator for a plurality of number of times with changing a storage time;

a sub-thickness image forming device for forming sub-thickness images corresponding to the respective plurality of the transmission images of different storage times supplied from the imaging device on the basis of a relationship between a brightness density of the transmission image and a thickness of the connected part; and a superimposed image forming device for forming a thickness superimposed image of the connected part by adding the plurality of the sub-thickness images to each other.

The above superimposed image forming device may be configured to extract and collect only valid parts of the plurality of sub-thickness images respectively so as to form the thickness superimposed image.

The image forming device can first form sub-thickness images corresponding to the respective transmission images at the storage times when one connected part is present along an application direction of the radiation, and also forms second sub-thickness images corresponding to each of the transmission images at the different storage times in a state with the connected parts overlapping when a plurality of the connected parts are present overlapping in the application direction of the radiation, while the superimposed image forming device forms a first thickness superimposed image by adding a plurality of the first sub-thickness images to each other and also forms a second thickness superimposed image by adding a plurality of the second sub-thickness images to each other, and subtracts the first thickness superimposed image from the second thickness superimposed image so as to form the thickness superimposed image.

When the connected parts are present at one and the other face opposite to each other of a plate-shaped member, the first thickness superimposed image formed by the image forming device may correspond to the connected part at the one face, and the second thickness superimposed image corresponds to the connected parts at both the one and the other face. The thickness superimposed image of the connected part at the other face can be obtained by subtracting the first thickness superimposed image from the second thickness superimposed image.

Also, the superimposed image forming device can be adapted to extract and collect only valid parts from the plurality of first sub-thickness images respectively so as to form the first thickness superimposed image, and moreover extract and collect only valid parts from the plurality of second sub-thickness images so as to form the second thickness superimposed image.

The relationship between the brightness density of the transmission images and the thickness of the connected part can be obtained with the use of a teaching jig of a known thickness which is formed of a material with a radiation transmittance equal to the connected part.

A connection inspecting method according to a second aspect of the present invention, comprises:

applying radiation to the connected part of members with an application condition kept invariant, and then converting the radiation passed through the connected part to a visible light;

picking up transmission images of the connected part expressed by the visible light for a plurality of number of times with changing a storage time;

forming sub-thickness images corresponding to the respective plurality of the transmission images of different storage times on the basis of a relationship between a brightness density of the transmission image and a thickness of the connected part; and forming a thickness superimposed image by adding the plurality of sub-thickness images to each other so as to inspect the connected part.

According to a third aspect of the present invention, a recording medium for recording programs executing the connection inspecting method of the above second aspect is provided. The recording medium comprises:

a process of applying a radiation to a connected part of members with an application condition kept invariant, and converting the radiation passed through the connected part to visible light;

a process of picking up transmission images of the connected part expressed by the visible light for a plurality of the number of times with changing a storage time;

a process of forming sub-thickness images corresponding to the respective transmission images of the different storage times on the basis of a relationship between a brightness density of the transmission image and a thickness of the connected part; and a process of adding the plurality of sub-thickness images to each other so as to form a thickness superimposed image.

As described above, according to the connection inspecting apparatus of the first aspect, connection inspecting method of the second aspect, and recording medium of the third aspect of the present invention, there are provided the sub-thickness image forming device and the superimposed image forming device, whereby sub-thickness images are formed corresponding to a plurality of transmission images of different storage times at respective storage times on the basis of the relationship between the brightness density of the transmission image and the thickness of the connected part, so that the thickness superimposed image of the connected part is formed by adding the plurality of sub-thickness images. Each of the sub-thickness images includes no part exceeding a dynamic range of an image density and no part not larger than a minimum image density signal, thus enabling highly accurate inspection of the thickness of the connected part by the addition of the sub-thickness images.

The thickness superimposed image can be formed also by extracting only valid parts from the respective sub-thickness images. The thickness of the connected part can accordingly be highly accurately inspected over a limit of the dynamic range of the image density of an image pickup system.

As an applied operation of the above, an arrangement is constituted so that a first thickness image is first obtained, then a second thickness image is obtained, and a thickness superimposed image is obtained by subtracting the first thickness image from the second thickness image, whereby the thickness of each of a plurality of the connected parts overlapping along an application direction of radiation can even be highly accurately inspected.

A connection inspecting apparatus according to a fourth aspect of the present invention comprises:

an irradiation device for applying radiation to a connected part;

a scintillator for converting the radiation passed through the connected part to a visible light;

an imaging device for picking up a transmission image of the connected part generated from the scintillator; and an image forming device for forming brightness information on the basis of the transmission image supplied from the imaging device of a first connected part and a second connected part of an object to be inspected which overlap at a part in a thicknesswise direction thereof, and for forming an image of only the second connected part on the basis of the brightness information.

The image forming device can form the image of only the second connected part also by binarizing the brightness information by a bright side level (A+α) brighter than a reference brightness level (A) of the transmission image of the first connected part when the object includes only the first connected part and by a dark side level (A−β) darker than the reference brightness level.

Based on an image of the overlapping first connected part and second connected part obtained by binarizing the brightness information, an image of only the first connected part obtained by the binarization by the bright side level, and an image of the overlapping part obtained by the binarization by the dark side level, the image forming device can form the image of only the second connected part by deleting the image of only the first connected part from the image of the first and second connected parts, and adding the image of the overlapping part to an image after the deletion.

The image forming device can obtain outline position information of the first connected part based on the transmission image of the first connected part, thereby forming the image of only the second connected part on the basis of the brightness information and the outline position information.

Furthermore, the image forming device can detect a brightness change at an outline position indicated by the outline position information with the use of the brightness information, obtain each position information of one position and the other position in an outline segment of the overlapping part showing a different brightness change from other positions, obtain information on a divide line passing the one position and the other position from the position information, and form the image of only the second connected part from the brightness information by changing a binarization level at a first region including the first connected part and a second region including the second connected part which are divided by the divide line.

The binarization level at the divided first region including the first connected part may be set to a level for extracting only the overlapping part, while the binarization level at the second region including the second connected part may be rendered a brightness level of the second connected part obtained when each position information of the one position and the other position is obtained.

The image forming device may obtain each position information of the one position and the other position on the basis of a peak value of the brightness in place of the brightness change.

The imaging device can pick up the image of the first connected part and the second connected part in the overlap state with changing an image storage time.

The imaging device can pick up images of the first connected part and the second connected part in the overlap state with changing an image storage time, so that the image forming device obtains the one position and the other position in the outline segment of the overlapping part with the use of the brightness information of a largest brightness change among the brightness information of transmission images for every one of different storage times.

The image forming device can obtain each position information of the one position and the other position on the basis of the brightness information of a largest peak value of the brightness in place of the brightness information of the maximum brightness change.

A connection inspecting method according to a fifth aspect of the present invention comprises:

applying radiation to an object to be inspected which has a first connected part overlapping with a second connected part at a part in a thicknesswise direction of the object, and converting the radiation passed through the object to visible light;

forming brightness information on the basis of a transmission image of the first connected part and the second connected part in the overlap state which is obtained through the conversion to the visible light; and forming an image of only the second connected part on the basis of the brightness information.

In the connection inspecting method of the fifth aspect, the operation of forming the image of only the second connected part may be carried out by:

binarizing the brightness information, thereby obtaining an image of the first connected part and the second connected part in the overlap state;

binarizing the brightness information by a bright side level (A+α) brighter than a reference brightness level (A) at a transmission image of the first connected part when the object has only the first connected part, thereby obtaining an image of only the first connected part;

binarizing the brightness information by a dark side level (A−β) darker than the reference brightness level, thereby obtaining an image of the overlapping part; and deleting the image of only the first connected part from the image of the first connected part and the second connected part, and adding the image of the overlapping part to an image after the deletion.

A recording medium for recording programs executing a connection inspecting method in a sixth aspect of the present invention is provided with a process of applying a radiation to an object to be inspected which has a first connected part overlapping with a second connected part at a part in a thickness direction of the object;

a process of forming brightness information based on a transmission image of the first connected part and the second connected part in the overlap state which is obtained by converting a radiation passed through the object to a visible light; and a process of forming an image of only the second connected part on the basis of the brightness information.

As discussed above, according to the connection inspecting apparatus in the fourth aspect, connection inspecting method of the fifth aspect, and recording medium of the sixth aspect of the present invention, the image forming device is provided, wherein the brightness information is formed on the basis of the picked image of the first connected part and the second connected part in the overlap state, based on which the image of only the second connected part is formed. A memory capacity can be reduced by converting the transmission image to brightness information instead of storing the transmission image directly as image information as in the related art. The memory capacity can be reduced further by storing an average brightness value of the brightness information.

Since the image of only the second connected part is formed by binarizing the brightness information formed on the basis of the picked image of the first and second connected parts in the overlap state by the bright side level and the dark side level, the need of registering the picked image of only the first connected part and the picked image of the first and second connected parts as in the related art is eliminated. The image of only the second connected part can be correctly formed even if the picked images deviate, etc. A reliability on inspection of the connected parts can be improved in comparison with the related art.

When the image of only the second connected part is obtained on the basis of the brightness information and outline position information, it becomes possible to obtain the image of only the second detect part from the transmission image of a so-called double face-mounted board even if the first connected part and second connected part are hardly different or equal in brightness. The reliability on inspection of the connected parts can be improved as compared with the related art.

In contrast to the case where the image of only the second connected part is obtained simply with the use of the outline position information, when the image of only the second connected part is obtained on the basis of the brightness peak value at the outline position, the image of the second connected part can be obtained more easily and can be processed in a reduced time. The reliability on inspection of the connected parts can be improved in comparison with the related art.

The image storage time is changed in picking up the overlapping first and second connected parts. Therefore, it is possible to pick up and obtain images of the first and second connected parts even if the first and second connected parts are extremely different in thickness. The reliability on inspection of the connected parts can be improved in comparison with the related art.

DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF THE INVENTION

Figure 1:
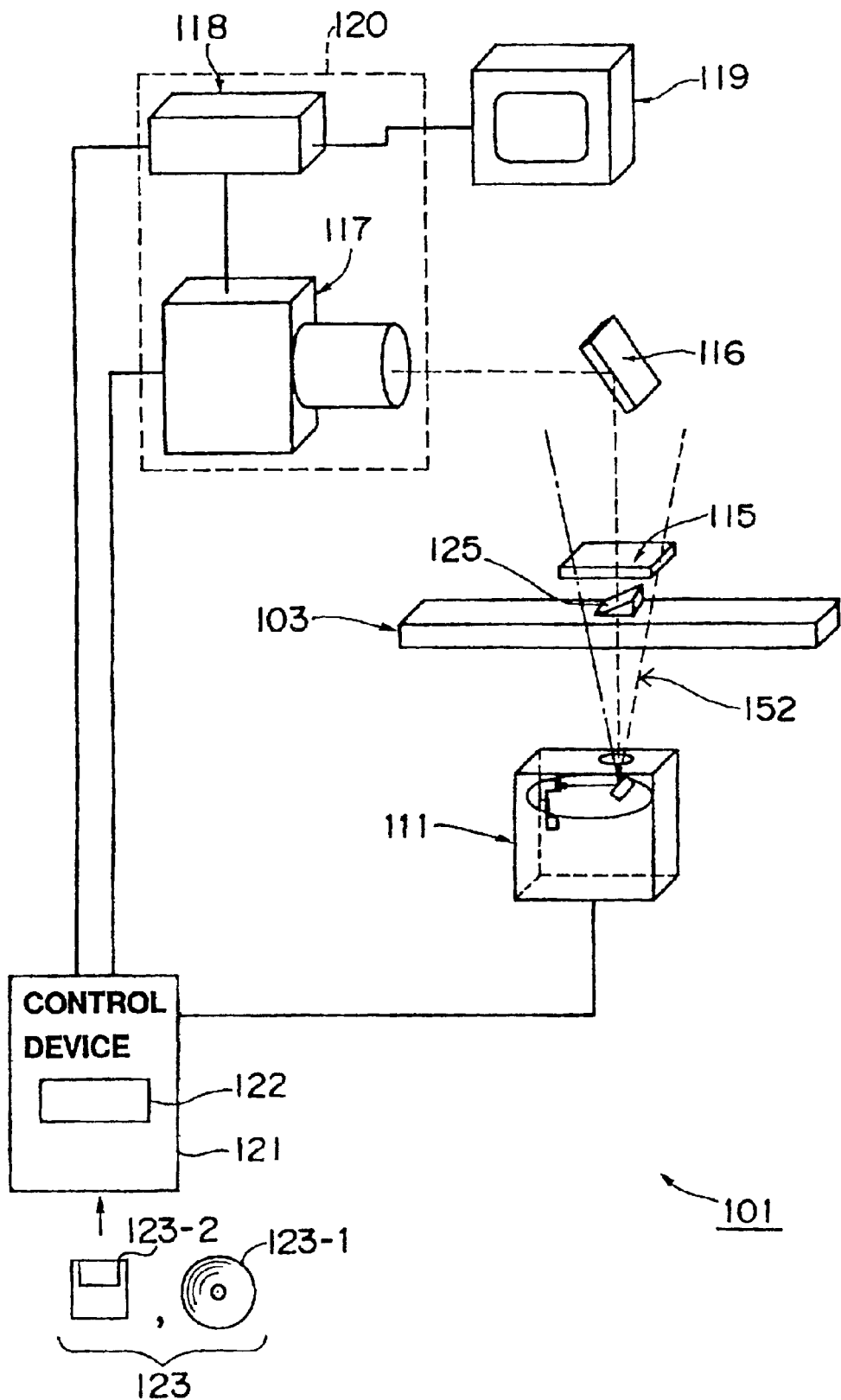
FIG. 1 is a diagram showing the constitution of a connection inspecting apparatus according to a first embodiment of the present invention.

A connection inspecting apparatus, a connection inspecting method, and a recording medium for recording programs executing a connection inspecting method which are embodiments of the present invention will be described hereinbelow with reference to the drawings. It is to be noted that like parts are designated by like reference numerals throughout the drawings.

According to the embodiments, the connection inspecting apparatus, connection inspecting method, and recording medium for recording programs executing the connection inspecting method are provided, whereby limits on a dynamic range of an image density and a resolution of a pickup system are overcome. In other words, a height of a connecting material can be measured regardless of a thickness of an object to be inspected, and double face-mounted circuit boards can be inspected as well, thereby improving an inspection accuracy for connected parts of mounted components in comparison with the related art.

While X-rays are exemplified in each of the following embodiments as the "radiation" described in the above "SUMMARY OF THE INVENTION", the "radiation" is not restricted to X-rays and can be gamma rays or the like. A control device 121 represents in each embodiment below an example functioning as the "sub thickness image forming device" and "superimposed image forming device" depicted in the above "SUMMARY OF THE INVENTION". Moreover, although a connected part between an electrode of a circuit board and an electrode of an electronic component in the electronic component mounted onto the circuit board is discussed as an example of the "connected part of members" described in the "SUMMARY OF THE INVENTION", the connected part is not limited to this and conceptually includes, e.g., a connected part between a plurality of electronic components or the like.

First Embodiment

As shown in FIG. 1, a connection inspecting apparatus 101 according to a first embodiment roughly comprises an X-ray generator 111 as an example functioning as an irradiation part, an X-ray scintillator 115, an image pickup device 120, and a control device 121. The image pickup device 120 includes a camera 117, and an image-processing device 118 to which picked information sent from the camera 117 is supplied.

The X-ray generator 111 produces X-rays 152 to be applied to a mount part where an electronic component 104 is mounted on a circuit board 103 by a connecting component side electrode formed to a rear face of the electronic component 104 and a mount side electrode formed to the circuit board 103 to which the electronic component 104 is to be mounted. Although the X-rays 152 are applied to a range of the mount part according to the first embodiment, it is enough to apply the X-rays to at least a range of a connected part between the component side electrode and the mount side electrode.

In the first embodiment, the X-ray generator 111 produces X-rays 152 by an output of approximately 50 kV–200 kV, e.g., 90 kV and approximately 0.5 mA.

The X-ray scintillator 115 converts X-rays passing through the mount part to visible light having a quantity of light proportional to an X-ray intensity of the passing X-rays. At this time, X-rays 152 are attenuated in accordance with a thickness of at least one substance through which the X-rays pass, and an X-ray absorption coefficient of the substance. Therefore, an X-ray image according to a quantity of attenuation of X-rays at each part of the mount part 115 between the circuit board 103 and electronic component 104 is projected to the X-ray scintillator 115. The X-ray scintillator 115 produces visible light corresponding to the X-ray image.

The visible light produced from the X-ray scintillator 115 is reflected at a mirror 116 and brought into the camera 117. Setting the mirror 116 in this manner is to bring the camera 117 outside an application range of X-rays, thereby avoiding damage to the camera 116 because of direct application of X-rays.

The image of the mount part picked up by the camera 117 is processed by the image-processing device 118. Since a heavy metal material such as lead, tin or the like having a high index of absorption to X-rays is generally used for the connected part between the component side electrode of the electronic component 104 and the mount side electrode of the circuit board 103, the connected part is displayed dark in contrast to a peripheral part among the mount part when the visible light corresponding to the transmission image by the X-rays is processed. The connected part and its peripheral part can thus be distinguished from each other. The image, after being processed is sent to the control device 121 and a monitor TV 119 which is an example of a display device.

The control device 121 is connected to the above X-ray generator 111, camera 117, and image-processing device 118, controlling operations of these devices and generating thickness information of the connected part among the mount part as will be described later.

The operation in the connection inspecting apparatus constituted as above will be discussed hereinbelow, which is controlled by the control device 121.

Figure 2:
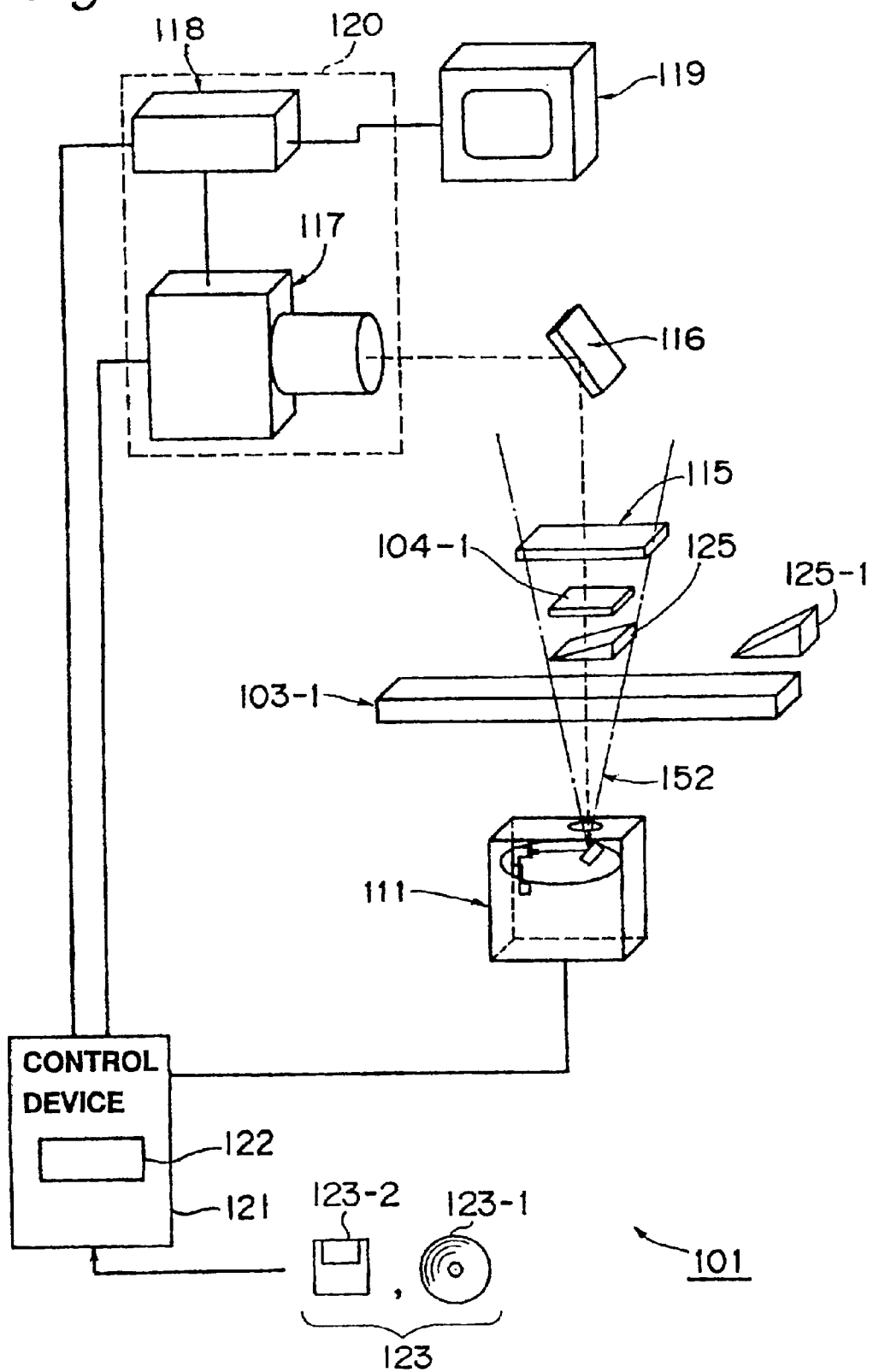
FIG. 2 is a diagram explanatory of the operation for obtaining a relationship between a brightness density and a thickness of a connected part in a transmission image before carrying out an inspection by the connection inspecting apparatus of FIG. 1.
Figure 6:
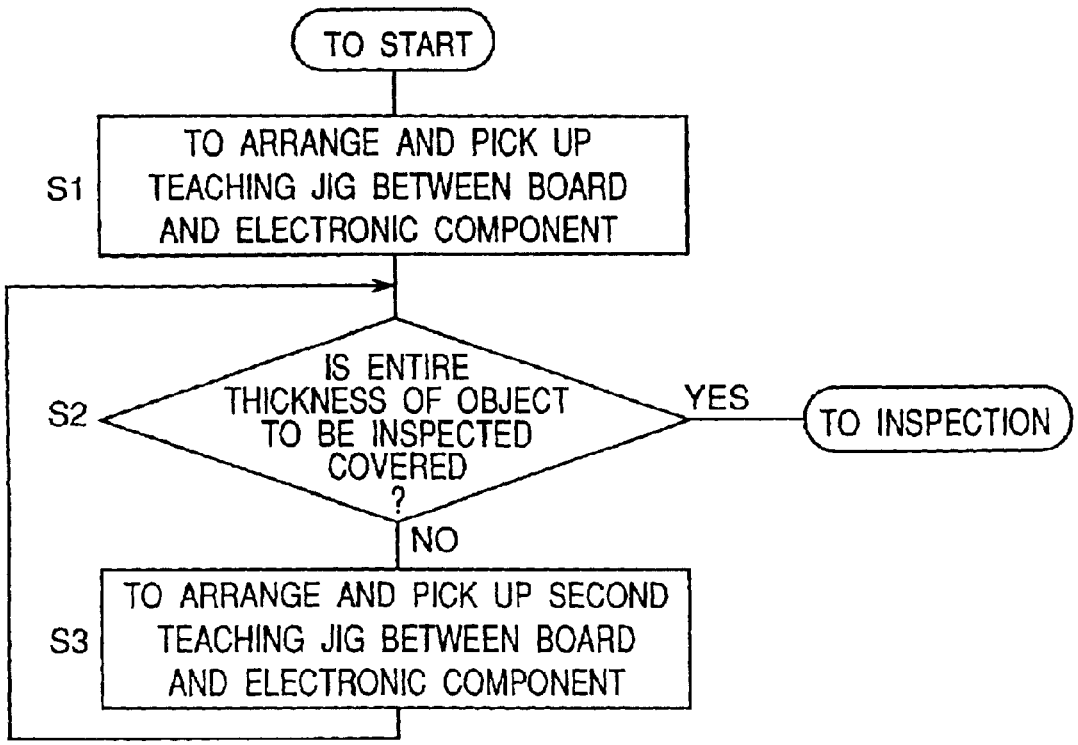
FIG. 6 is a flow chart of the operation for obtaining the image density and the transmission substance thickness in the first embodiment of the present invention.

In step (designated by "S" in drawings) 1 of FIG. 6, in an inspection preparation prior to formally inspecting the connected part between the circuit board and the electronic component, a circuit board 103-1 and an electronic component 104-1 before connection are prepared beforehand, and a staircase-shaped teaching jig 125 is disposed between the circuit board 103-1 and electronic component 104-1 as shown in FIG. 2.

Figure 3:
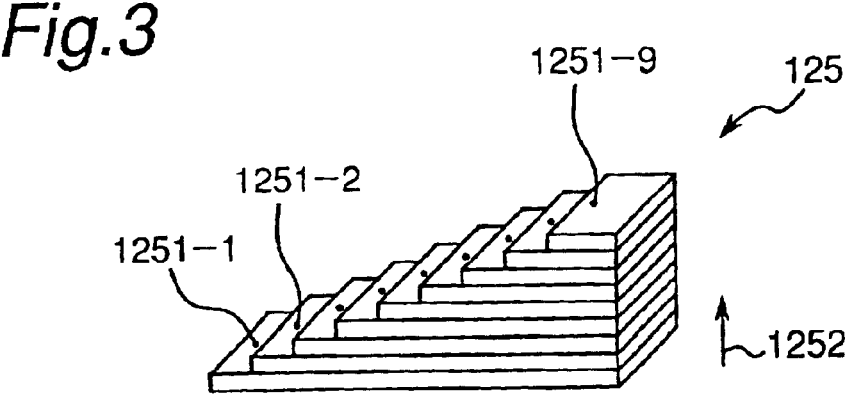
FIG. 3 is a perspective view of a teaching jig of FIG. 2.

The teaching jig 125 is formed of the same material as the connected part between the component side electrode and the mount side electrode and into the shape of, e.g., a staircase, a wedge or the like with a plurality of measurement points 1251-1, 1251-2, . . . as shown in FIG. 3. The teaching jig 125 varies in thickness along a transmission direction 1252 of the X-rays, i.e., thicknesswise direction thereof while each thickness is known. Although the teaching jig 125 in the first embodiment has nine measurement points 1251-1 to 1251-9, the number of measurement points where the thickness varies is not limited to this. That the teaching jig 125 is formed of the same material as the connected part means that the teaching jig has an X-ray transmittance equal to that of the connected part. Specifically, the teaching jig has component substances and a content of the component substances equal to those of the connected part.

Figure 4:
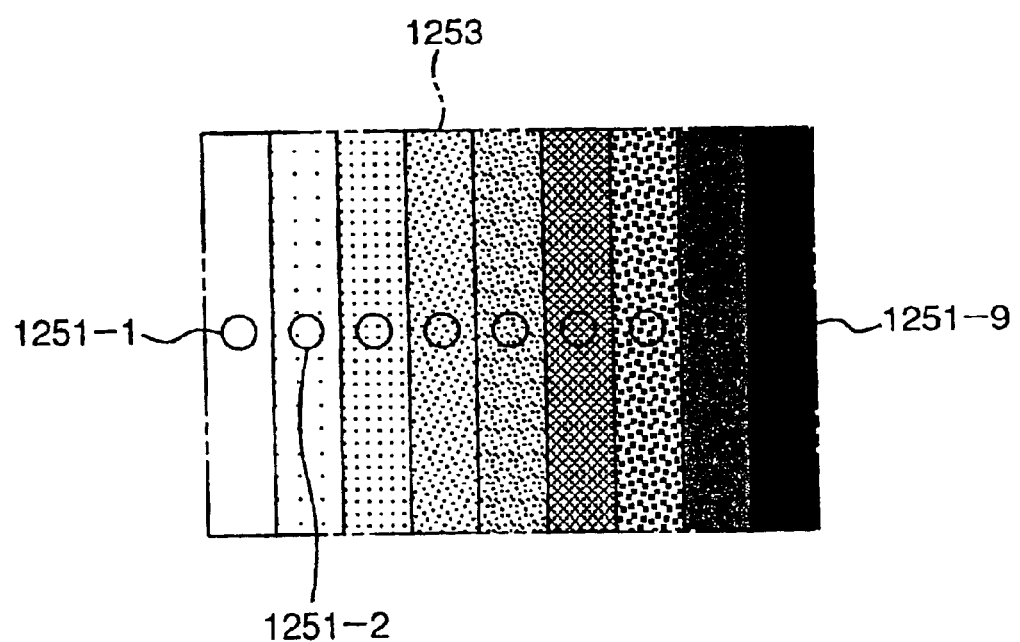
FIG. 4 is a diagram of an X-ray image of the teaching jig when picked up by the connection inspecting apparatus of FIG. 2.
Figure 5:
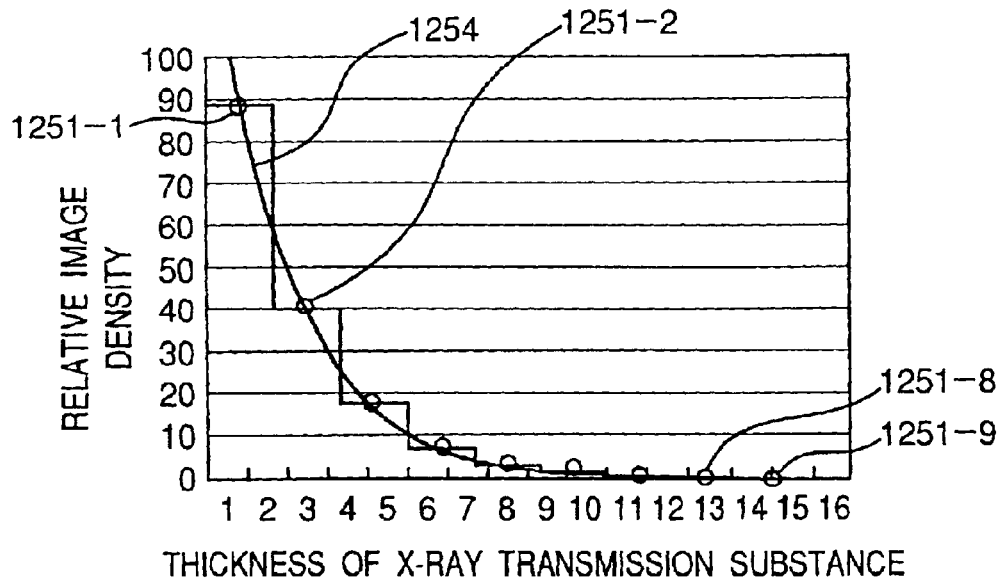
FIG. 5 is a graph showing a relationship between a density of the image formed by the connection inspecting apparatus of FIG. 1 and a thickness of a transmission substance.

In the above arrangement, X-ray pickup is carried out with an X-ray application condition such as a tube voltage, a tube current and the like of the X-ray generator 111, and a storage time of the transmission image formed by the visible light at the camera 117 being kept constant. The X-ray image by the X-ray pickup becomes, as indicated in FIG. 4, an image of stepwise density differences corresponding to thicknesses of the teaching jig 125. An image density of each of the measurement points 1251-1 to 1251-9 of the known thicknesses of the teaching jig 125 is measured by the image-processing device 118, and formed to a graph in which the thickness of the X-ray transmission substance is represented on an abscissa and the image density is represented on an ordinate. A logarithmic graph as shown in FIG. 5 is obtained by plotting and connecting each density value of the measurement points to an approximate curve.

In step 2, it is judged whether or not a thickness range to be inspected of the connected part is covered by the teaching member 125. The process moves to an inspection to be described later when the range is covered, whereas the process goes to next step 3 unless the range is covered. In other words, given that the thickness range of the connected part to be inspected is, for instance, from 100 μm to 1500 μm although the teaching member is able to cover only a range of 100 μm to 500 μm, a second and a third teaching members for covering, e.g., a range of 500 μm to 1000 μm and a range of 1000 μm to 1500 μm, respectively, are needed. The step moves to step 3 when a plurality of teaching members are required as above.

In step 3, a staircase-shaped or wedge-shaped second teaching jig 125-1 having a thickness range to cover the whole or part of the thickness range not covered by the above teaching jig 125 is set between the circuit board 103-1 and electronic component 104-1 in place of the teaching jig 125. X-ray pickup is carried out without changing the X-ray application condition such as the tube voltage, tube current, etc. of the X-ray generator 111 and with adjusting the storage time at the camera 117 to meet a thickness change by the teaching jig 125-1.

An X-ray image when the teaching jig 125-1 is used is similar to the image of FIG. 4, that is, the image has density differences generated stepwise corresponding to thicknesses of the teaching jig 125-1. An image density at each measurement point of the known thickness of the teaching jig 125-1 is measured by the image-processing device 118 and formed into a graph in which the thickness of the X-ray transmission substance is represented on the abscissa and the image density is represented on the ordinate. A logarithmic graph similar to the graph of FIG. 5 is formed by connecting each density value of the measurement points to plot to an approximate curve.

In the manner as discussed above, the teaching jigs of different thickness ranges are sequentially used to form the logarithmic graphs until the entire thickness range of the connected part is covered.

In order to inspect each of equal connected parts, for example, in order to inspect a plurality of products having equal electronic components mounted on equal circuit boards, practically, data of the preliminarily obtained logarithmic graphs are stored in a storage 122 of the control device 121 and read out when used. Supplying from a recording medium such as a floppy disk or the like, supplying with the use of a communication line, or the like known method can be employed to store the logarithmic graph data.

The inspection of the connected part between the circuit board and electronic component after the above-described preparation stage will be depicted. The description below is directed to an example where one connected part is picked up with the use of a plurality of teaching jigs 125. In step 5 in FIG. 7, X-ray pickup is conducted by a plurality of the number of times to the connected part with the same X-ray application condition and the same storage time condition of the camera 117 as when each of the above teaching jigs 125, 125-1, etc. is used to measure the connected part.

In next step 6, X-ray images obtained in step 5 corresponding to each teaching jig 125, etc. are respectively converted to sub-thickness images based on the preliminarily obtained logarithmic graphs as discussed hereinabove and image densities of the X-ray images at the connected part corresponding to the logarithmic graphs.

In the following step 7, regarding a plurality of the sub-thickness images, only valid parts are extracted respectively from the plurality of sub-thickness images in every measurement range of the image on the basis of a sub-thickness image which covers the thickness of a largest measurement range. The valid parts are collected, whereby a thickness superimposed image is formed.

Whether it is a good product or faulty product can be judged by comparing a thickness of an inspection point obtained from the above superimposed image with a thickness of a good product. Information on the thickness of the good product is stored into the storage 122 of the control device 121 beforehand in the first embodiment.

Figure 8:
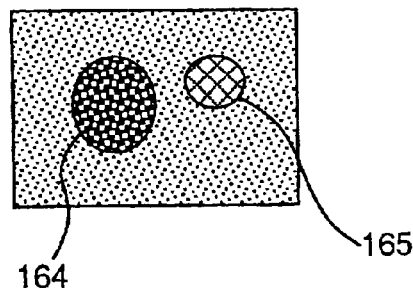
FIG. 8 is a diagram of a sub-thickness image of FIG. 7.
Figure 9:
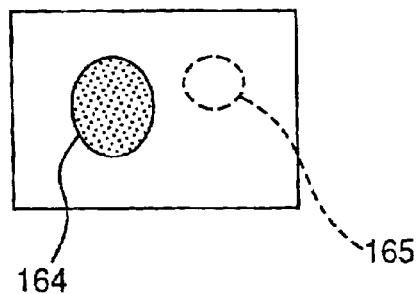
FIG. 9 is a diagram of the sub-thickness image of FIG. 7.

The operation in step 7 will be specifically described in conjunction with an example. The sub-thickness image obtained from the X-ray image with the storage time of T1 is indicated in FIG. 8, and the sub-thickness image obtained from the X-ray image with the storage time of T2 longer than T1 is shown in FIG. 9. A region 164 in FIG. 8 has the image density of a minimum level or lower and cannot be used. On the other hand, a region 165 in FIG. 9 has the image density exceeding a dynamic range and is saturated. In this case, the thickness image of FIG. 9 is extracted as the valid part for the region 164 and the thickness image of FIG. 8 is extracted as the valid part for the region 165 based on the sub-thickness image which covers the thickness of the largest measurement range. The extracted parts are collected, thereby forming the thickness superimposed image.

According to the first embodiment as above, the sub-thickness images are formed corresponding to X-ray images of different storage times, from which valid parts are extracted, respectively, and synthesized to produce the thickness superimposed image. More specifically, the X-ray image of a thin object exceeds the dynamic range of the image density and is saturated if the X-ray storage time is secured long enough to fit a thick object. In contrast, the X-ray image of the thick object has a minimum density signal or lower when the X-ray storage time is made short enough to fit the thin object. As such, only valid images which are not saturated and exceed the minimum density signal are extracted from the sub-thickness images and then the extracted valid images are synthesized, thereby generating the thickness superimposed image. Therefore, the thickness of the connected part can be highly accurately inspected with limits on the dynamic range of the image density and resolution of the pickup system being overcome.

Respective valid parts are extracted for the plurality of sub-thickness images and, the extracted valid parts are collected to form the thickness superimposed image in the first embodiment as above. However, the embodiment is not limited to the arrangement. For instance, if a maximum value of the thickness of a part to be inspected of the connected part is, e.g., within two times a minimum value, respective sub-thickness images are not greatly different in density. In such a case, the sub-thickness images are simply added without extracting the valid parts, thereby being able to form the thickness superimposed image.

In this simple manner as compared with the above-described way of extracting valid parts, the thickness of the connected part can be highly accurately inspected over the limit of the dynamic range of the image density in the pickup system.

Second Embodiment

The above-discussed first embodiment relates to the case where the electronic component 104 is mounted to one face of the circuit board 103. A second embodiment will handle the case where electronic components 104 are mounted to each of two faces of the circuit board 103.

Figure 10:
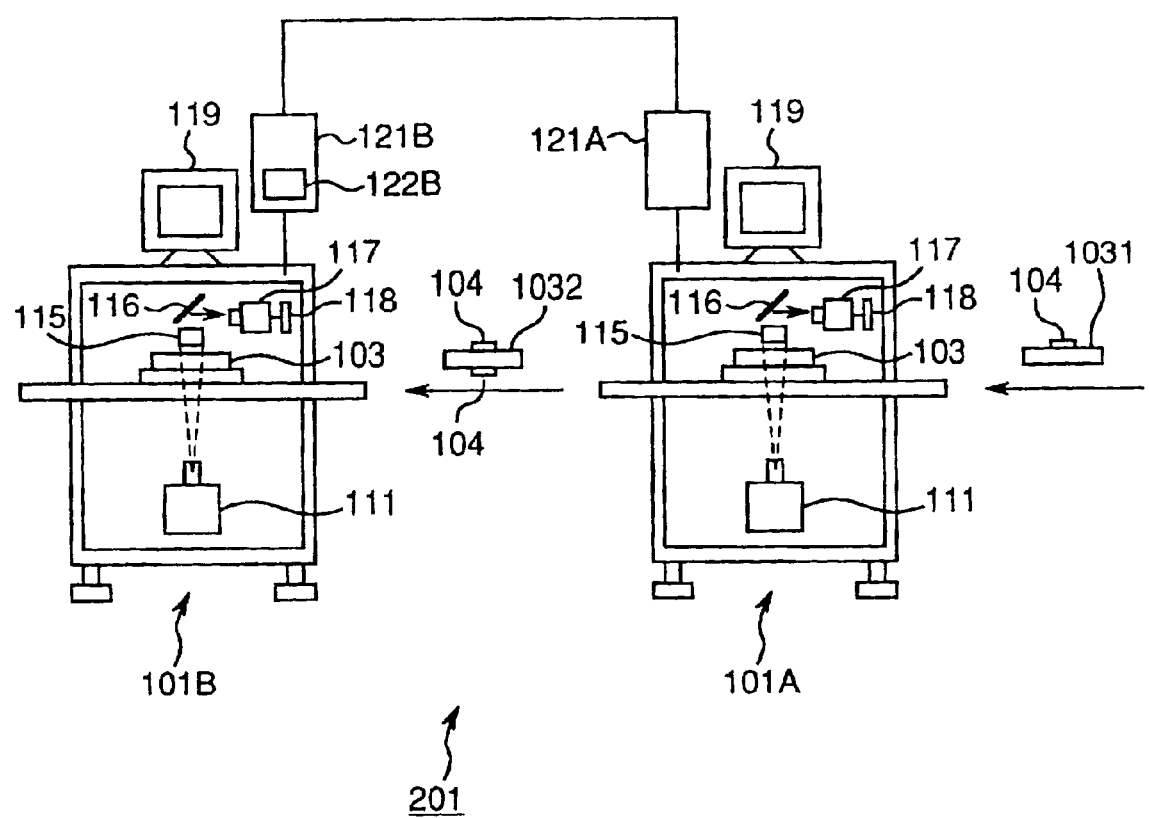
FIG. 10 is a diagram of the constitution of a connection inspecting apparatus according to a second embodiment of the present invention.

FIG. 10 shows a connection inspecting apparatus 201 according to the second embodiment. As is indicated in FIG. 10, in two connection inspecting machines 101A and 101B with the function of the earlier-described connection inspecting apparatus 101, a control device 121A corresponding to the control device 121 which is set to the connection inspecting machine 101A, and a control device 121B corresponding to the control device 121 which is set to the connection inspecting machine 101B are connected with each other. The connection inspecting apparatus 201 of this constitution enables inspection of the connected parts when the electronic components 104 are mounted to both faces of the circuit board 103. Briefly speaking, the connection inspecting apparatus 201 operates in a manner as follows.

Suppose that one face of the circuit board 103 is an A face and the other opposite face is a B face in the case of a double face mounting process for electronic components 104, the electronic component 104 is mounted to only one face of the circuit board 103 in an A face mounting process of mounting the electronic component 104 on the A face. In this state, the connected part can be inspected by the X-ray inspection method described in the first embodiment. However, when the circuit board 103 is turned upside down and the electronic component 104 is mounted to the B face, there are two connected parts along the application direction of X-rays because the electronic component 104 is already mounted on the A face of the circuit board 103. As a result, the X-ray image becomes an image in which the connected part at the A face and the connected part at the B face overlap, and is hard to inspect due to this.

For solving this problem, the X-ray image of the A face by the X-ray inspecting machine 101A is inverted along with the upside-down turning of the board and subtracted from the X-ray image of the B face by the X-ray inspecting machine 101B, so that the X-ray image of only the B face is extracted and then inspected. However, since densities of the X-ray images are expressed by logarithmic functions of the thicknesses of the transmission substance, it is impossible to extract only the image of the B face by the simple subtraction of the densities of the X-ray images.

Therefore, the subtraction is carried out with the sub-thickness images formed by logarithmically converting the X-ray images. A board ID by a bar code or the like is printed onto the circuit board 103 so as to match the A face image and the B face image. The board ID read by the A face inspecting machine 101A is transmitted together with the sub-thickness image of the A face to the B face inspecting machine 101B. The B face inspecting machine 101B subtracts the sub-thickness image by the A face inspecting machine 101A from the sub-thickness image by the B face inspecting machine 101B and then performs the inspection when a board IC read by the B face inspecting machine 101B from the board to be inspected agrees with the board ID sent from the A face inspecting machine 101A.

The inspection will be described with the use of FIG. 11. An A face-mounted circuit board 1031 of which the electronic component 104 is already mounted on the A face is supplied in step 11 of procedures in the A face inspecting machine 101A of FIG. 11. X-rays are applied in step 12 to the circuit board 1031 under the same X-ray application condition as when the teaching jig 125 is used to measure. The circuit board 1031 is picked up with X-rays under the same condition as the storage time condition of the camera 117 when the teaching jig 125 is used, and the X-ray image is inputted in step 13. In next step 14, the X-ray image is converted to a sub-thickness image with the use of the logarithmic graph obtained beforehand for converting the image density to the thickness. X-ray images are obtained in step 15 for all of the plurality of pickup conditions set when the teaching jigs are measured. Steps 12–14 are repeated until the X-ray images are completely converted to sub-thickness images. A plurality of sub-thickness images are obtained in this manner.

As is discussed in the first embodiment, in next step 16, only valid parts are extracted from the plurality of the sub-thickness images according to the measurement ranges of each image based on the reference image which covers the thickness of the largest measurement range, and the extracted valid parts are gathered to obtain one thickness superimposed image of the A face.

The connection is inspected in step 17 by comparing shapes obtained from the thickness superimposed image of the A face and information on positions where the shapes are present, with preliminarily obtained information on thickness of the good product. In step 18, data of the thickness superimposed image of the A face and the board ID of the A face-mounted circuit board 1031 are transmitted to the B face inspecting machine 101B as shown in FIG. 10. The application of X-rays is stopped in step 19. Whether the production is to be continued or not is judged in step 20. The step returns to step 11 when the production is to be continued, so that steps 11–19 are repeatedly carried out.

Figure 11:
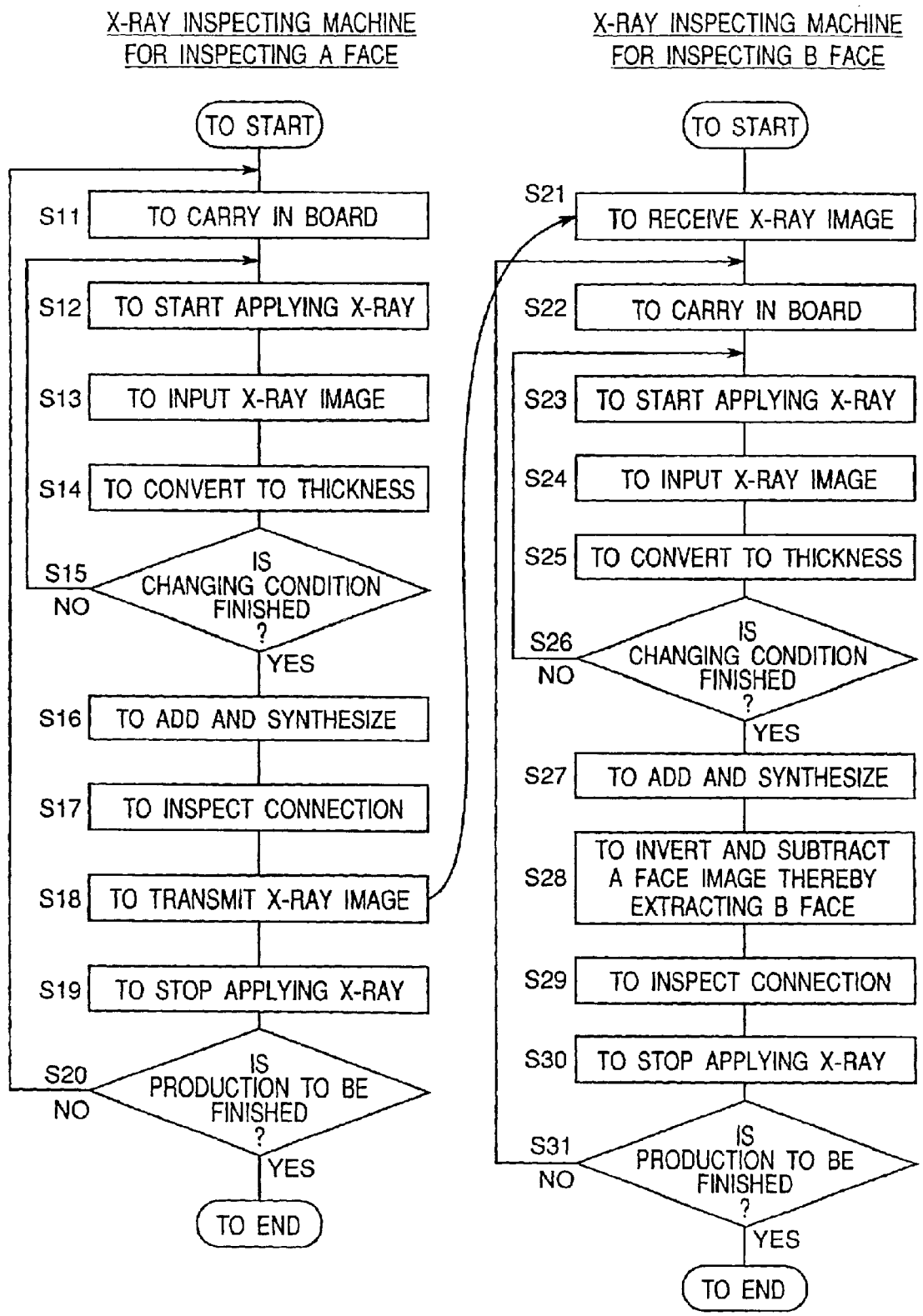
FIG. 11 is a flow chart of a connection inspecting operation carried out in the connection inspecting apparatus of FIG. 10.
Figure 12:
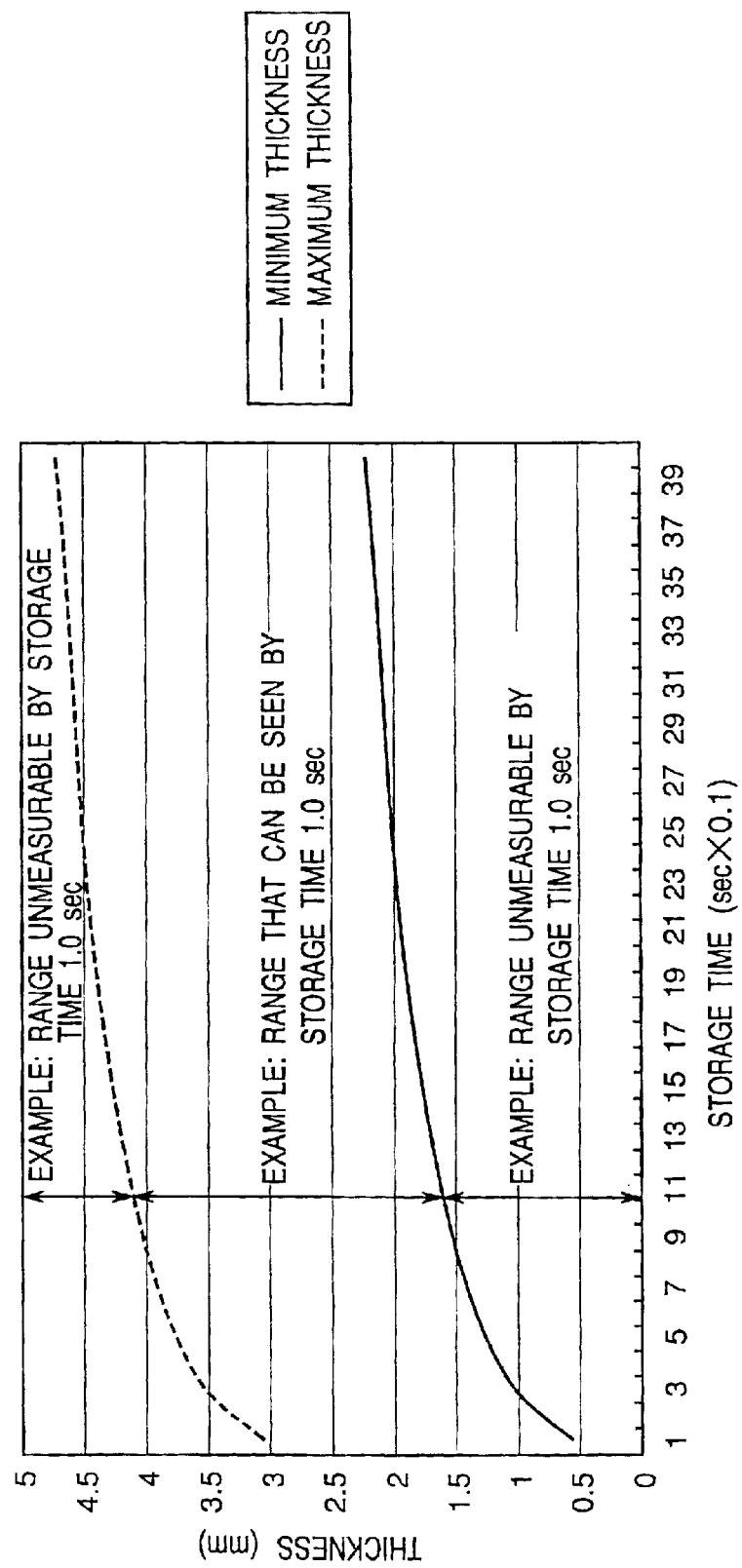
FIG. 12 is a diagram explanatory of problems in a conventional X-ray inspecting apparatus.

Meanwhile, in the inspection process of the B face inspecting machine 101B, in step 21, each data of the thickness superimposed image of the A face and the board ID supplied from the A face inspecting machine 101A beforehand is received and stored in a storage 122B of the control device 121B of the B face inspecting machine 101B as indicated in FIG. 11. A double face-mounted board 1032 with the electronic component 104 also mounted to the B face is carried into the B face inspecting machine 101B in step 22. X-rays are applied in step 23 to the double face-mounted board 1032 under the same X-ray application condition as when the supplied double face-mounted board 1032 is measured with the use of the teaching jig 125. The X-ray image of the double face-mounted board 1032 is inputted in step 24, and the X-ray image is converted to a sub-thickness image in step 25. X-ray images are obtained in step 26 for all of the plurality of pickup conditions executed when the teaching jigs are measured. Steps 23–25 are repeated until the conversion to sub-thickness images is complete. A plurality of sub-thickness images are obtained.

In step 27, similar to the above step 16, only valid parts are extracted from each of the plurality of sub-thickness images according to the measurement ranges of each image based on the image which covers the thickness of the largest measurement range, and the extracted valid parts are collected thereby obtaining one thickness superimposed image of double faces. In step 28, an image obtained by inverting data of the thickness superimposed image of the A face having the board ID matching with the board ID sent from the A face inspecting machine 101A, that is, an image obtained by inverting light and dark in the A face thickness superimposed image, is subtracted from the double face thickness superimposed image, thereby forming a B face thickness superimposed image of only the connected part of the B face.

In step 29, shape and position information obtained from the above B face thickness superimposed image are compared with preliminarily obtained thickness information of the good product, so that the connected part of the B face is inspected. Then the X-rays are stopped to be applied in step 30. Whether to continue the production is judged in step 31. The step returns to step 22 when the production is to be continued, and steps 22–30 are repeated.

As above, the connected part at each face of the double face-mounted circuit board can be inspected highly accurately over the limit of the dynamic range of the image density of the pickup system by applying the inspecting method of the first embodiment.

The circuit board is discussed by way of example and electronic components are mounted to both faces of the circuit board in the above second embodiment. This second embodiment is also applicable to a case, e.g., in which three or more components in a state of overlap in the application direction of X-rays are connected with each other. If the connected parts are, for instance, three parts, only a first thickness superimposed image is obtained for the first connected part, and then a second thickness superimposed image is obtained for a part where the first and second connected parts overlap. A thickness superimposed image for the second connected part can be obtained by subtracting the first thickness superimposed image from the second thickness superimposed image. Furthermore, a third thickness superimposed image is obtained for a part where the first, second and third connected parts overlap, from which the second thickness superimposed image is subtracted, whereby a thickness superimposed image for the third connected part is obtained. Even when a plurality of connected parts are present overlapping in the application direction of X-rays, the second embodiment can thus be applied accordingly.

So long as a maximum value of the thickness of a part to be inspected of the connected part is, e.g., within two times a minimum value of the thickness in the double face-mounted circuit board, sub-thickness images may be added simply to form the thickness superimposed image without executing the extraction of the valid parts. In this case, operations in steps 14 and 25 in FIG. 11 are omitted.

Figure 7:
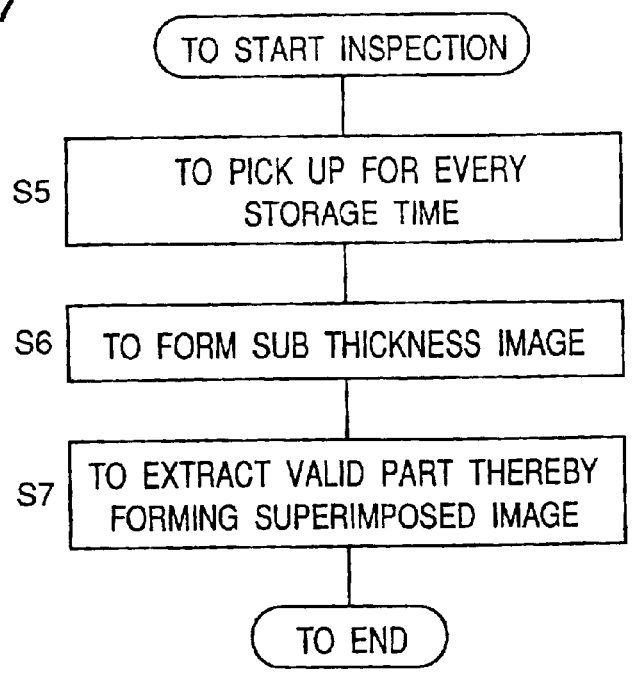
FIG. 7 is a flow chart of a connection inspecting operation in the first embodiment of the present invention.

The operation in the first embodiment described with reference to FIGS. 6 and 7 in the first embodiment, and the operation discussed with reference to FIG. 11 of the second embodiment are controlled in accordance with programs stored beforehand in the control device 121 or the like according to the first and second embodiments. The way of control is not limited to this. That is, it can be designed so that the control device 121 or the like reads out the programs for executing the operation discussed with reference to FIGS. 6 and 7 and the operation discussed with reference to FIG. 11 from a removable recording medium 123 such as a CD-ROM 123-1, a floppy disk 123-2 or the like having the programs stored therein, and executes a control operation in accordance with the read programs. Alternatively, the programs can be supplied to the control device 121 or the like with the utilization of a communication line.

Third Embodiment

In each of a third embodiment to a sixth embodiment to be described below, a component-mounted board with electronic components mounted to a printed board is adopted as an example of an object to be inspected. For example, a BGA (ball grid array), CSP (chip scale package) or the like flip chip component can be the electronic component. However, the object to be inspected is not restricted to this. The present invention is applicable to the case in which connected parts between a member to be mounted, i.e., the object to be inspected and the components overlap in a thicknesswise direction of the mount member and are hard to confirm or impossible to confirm from outside. In addition, although radiation to be applied to the object to be inspected is X-rays in the third-sixth embodiments, the radiation is not limited to X-rays.

Figure 13:
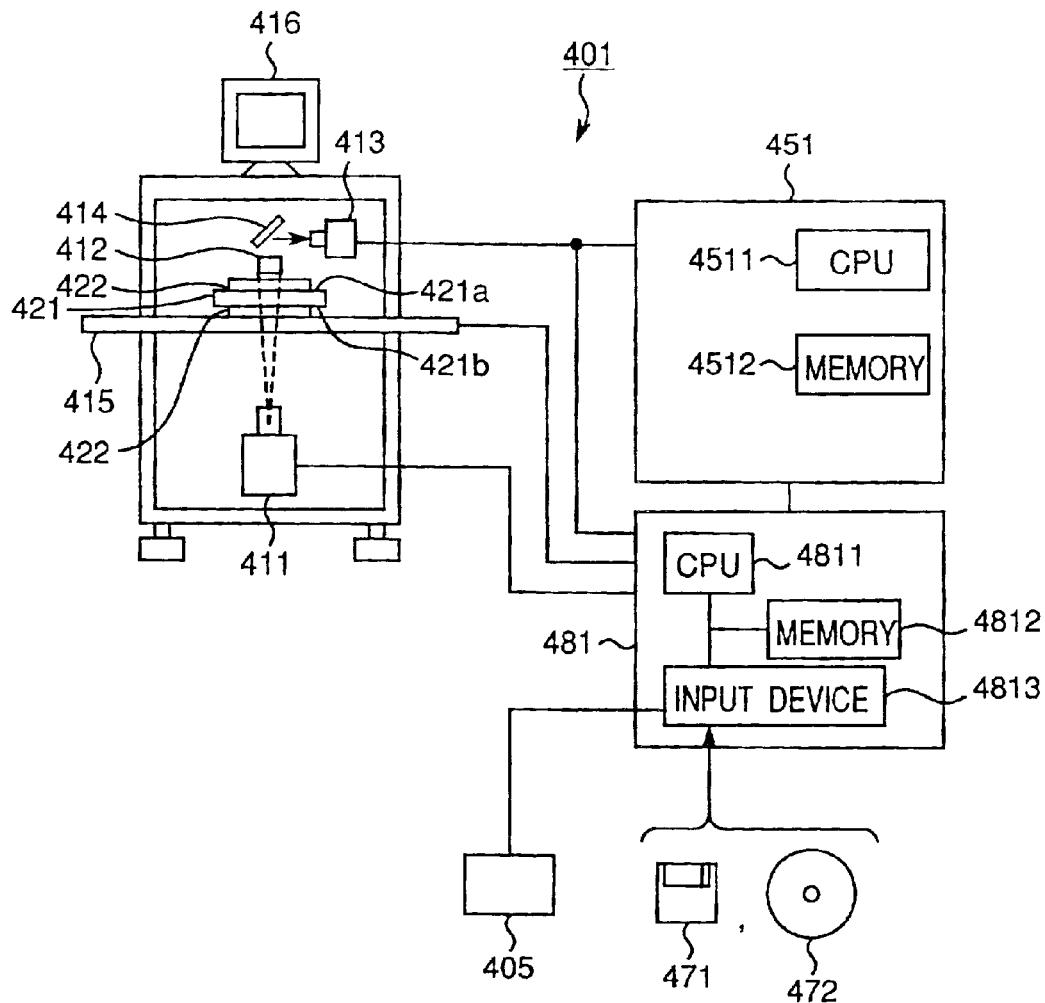
FIG. 13 is a diagram showing the whole constitution of a connection inspecting apparatus according to a third embodiment of the present invention.

A connection inspecting apparatus 401 in the third embodiment as shown in FIG. 13 includes an irradiation device 411, a scintillator 412, an image pickup device 413, a mirror 414 and a transfer device 415, and is also provided with an image forming device 451 and a control device 481 which are parts characterizing the connection inspecting apparatus 401. Although the image forming device 451 and control device 481 are indicated separately from a housing part which stores the irradiation device 411, etc. in FIG. 13, the image forming device 451 and control device 481 may be stored in the housing.

The irradiation device 411 applies X-rays of an intensity such that a transmission image of a connected part can be obtained to the connected part between an electronic component 422 and a printed board 421 in a thicknesswise direction or nearly thicknesswise direction of the printed board 421 having the electronic component 422 as an example of the component mounted in the third embodiment. FIG. 13 represents a case where electronic components 422 are mounted to a first face 421a and a second face 421b opposite to each other of the printed board 421, and moreover, X-rays are applied to an object to be inspected which has a first connected part at the first face 421a between the electronic component 422 and printed board 421, and a second connected part at the second face 421b between the electronic component 422 and printed board 421 positioned overlapping in the thicknesswise direction. However, the X-rays can be applied to an object which has the electronic component mounted only to the first face 421a. With respect to an X-ray application condition to the object, a storage time of the transmission image becomes longer for the double face-mounted board, i.e., the object with the electronic components 422 mounted to both the first face 421a and the second face 421b, than the object with the electronic component 422 mounted only to one face.

The scintillator 412 is a member for converting X-rays passing the connected part to visible light. The produced visible light is reflected by a mirror 414 and brought into the image pickup device 413. The pickup device 413 picks up the transmission image of the connected part by the visible light. The transfer device 415 is a device for transferring the printed board 421 with the electronic components 422 mounted thereon. A reference numeral 416 indicates a display device for visually displaying the inspection result or the like.

Figure 27:
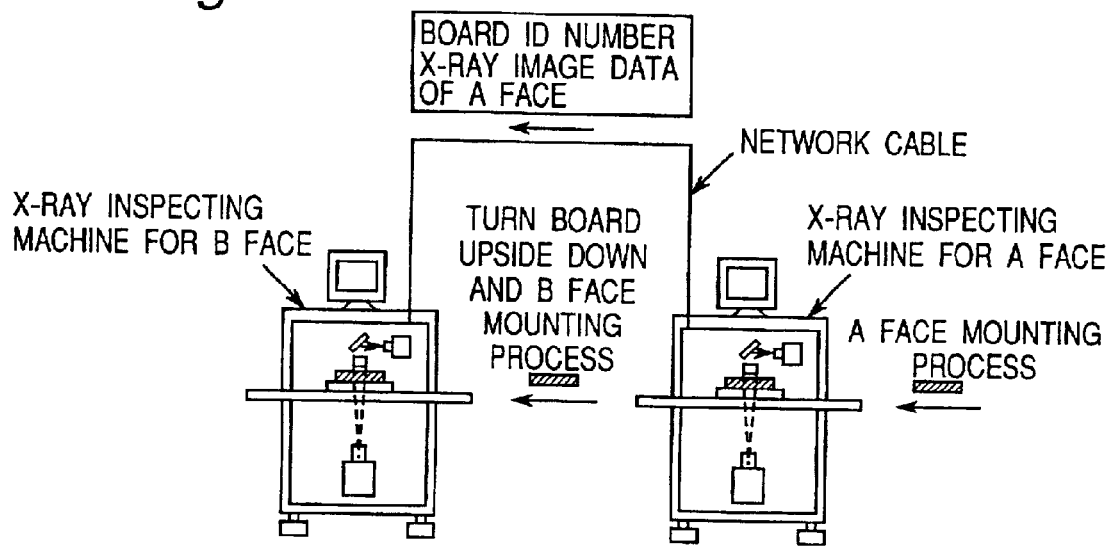
FIG. 27 is a diagram of the entire constitution of a conventional connection inspecting apparatus.
Figure 28:
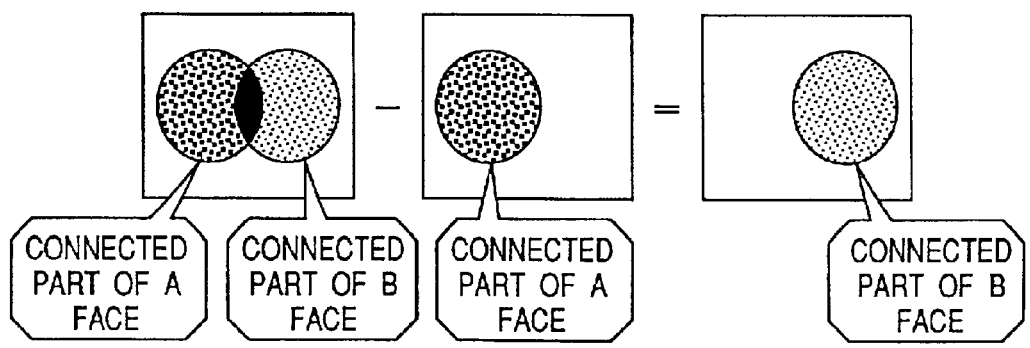
FIG. 28 is a diagram explanatory of a connection inspecting method carried out by the conventional connection inspecting apparatus.

The constitution including the above irradiation device 411, scintillator 412, image pickup device 413, mirror 414, transfer device 415, and display device 416 is the same as in the X-ray inspecting machine of FIG. 27.

Based on a transmission image of the first and second connected parts of the object including the overlapping part of the first connected part and second connected part, the transmission image being the picked image supplied from the image pickup device 413, the image forming device 451 including a CPU (central processing unit) 4511 and a memory 4512 converts the transmission image to information on, e.g., brightness of each pixel in the transmission image, not to the image information. The image forming device forms an image of only the second connected part based on the brightness information. The operation of the image forming device 451 will be detailed in a description of a connection inspecting method to be described later.

The control device 481 controls operations of the irradiation device 411, pickup device 413, transfer device 415, display device 416 and moreover of the image forming device 451. The control device 481 has the CPU 4811, the memory 4812 and an input device 4813. The input device 4813 to which is connectable another connection inspecting apparatus 405 can read a recording medium, for example, a floppy disk 471, a CD-ROM 472 or the like in which programs for executing a connection inspecting method in each of the third embodiment through the sixth embodiment to be described later are written. In the event that the programs are supplied by the recording medium, the programs read by the input device 4813 are stored to the memory 4812, thus enabling the CPU 4811 to execute each connection inspecting method.

The operation of the thus-constituted connection inspecting apparatus 401, namely, the connection inspecting method carried out by the connection inspecting apparatus 401 will be discussed below.

In the double face mounting process for electronic components, the electronic component 422 is mounted only to the first face 421a of the board 421 in a first mounting process. Effects of the second face 421b are not included in this state even when an image of the state is picked up with X-rays, because the electronic component 422 is not mounted to the second face 421b. However, when the board 421 is turned upside down and the electronic component 422 is mounted also to the second face 421b, there are mounted components on both faces of the board 421. Then, X-rays are applied to the board from the side of the second face 421b. An X-ray image shows two parts, i.e., the first connected part of the electronic component 422 mounted to the first face 421a, and the second connected part of the electronic component mounted to the second face 421b. Thus, inspecting the connected parts in this state is difficult.

Under the circumstances, the X-ray image of the first connected part is obtained in step (denoted by "S" in FIG. 17) 101 of the drawing by picking up the image from the second face 421b in a state while the electronic component 422 is mounted only to the first face 421a. The X-ray image is converted to the brightness information, and an average brightness value of the brightness information is obtained and stored to, for instance, the memory 4512 of the image forming device 451. The average brightness value corresponds to a level A of FIG. 15 to be depicted later. A memory capacity can be reduced because the transmission image is not directly stored as in the related art, but is stored after being converted to brightness information. The memory capacity can be furthermore reduced by storing the average brightness value of the brightness information.

In general, a plurality of boards of the same type are produced, and therefore, it is not necessary to obtain the brightness information of the X-ray image of the first connected part for every board. Instead, the brightness information and the average brightness value may be obtained for one sheet of a master board, so that the average brightness value of the master board can be used so long as boards of the same type as the master board are produced.

The above brightness information and average brightness value need not to be obtained by the connection inspecting apparatus 401 and may be supplied from the other connection inspecting apparatus 405, recording medium or the like.

According to the present third embodiment, the average value is used as the brightness information of the X-ray image of the first connected part. The brightness information is not limited to the average value and can be a variance, a maximum, a minimum or the like. In other words, a reference brightness level as a basis for obtaining a brightness level value with the use of $\alpha$ and $\beta$ values to be described later is enough.

Figure 14:
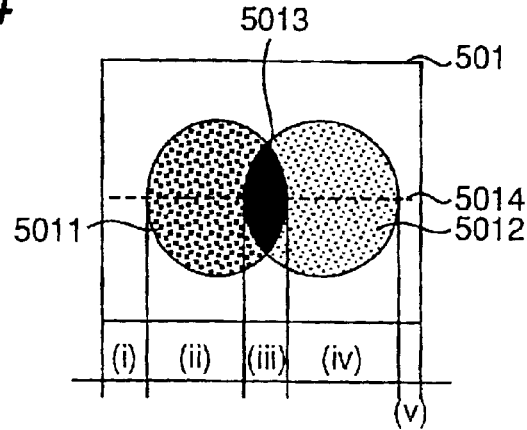
FIG. 14 is a diagram of a transmission image of a first connected part and a second connected part obtained by the connection inspecting apparatus of FIG. 13.

In step 102, the board having the electronic components 422 mounted to both of the first face 421a and second face 421b is supplied to the connection inspecting apparatus 401. In step 103, the double face-mounted board is picked up by the connection inspecting apparatus 401 from the side of the second face 421b. In step 104, the transmission image is obtained by the pickup device 413. An image of the first connected part and second connected part of one set of the transmission images is shown in FIG. 14. A reference numeral 5011 in the transmission image 501 in FIG. 14 indicates the first connected part which is a connected part of the electronic component 422 mounted on the first face 421a, while a reference numeral 5012 indicates the second connected part where the electronic component 422 mounted on the second face 421b is connected. The first connected part 5011 and second connected part 5012 have an overlapping part 5013. The first connected part 5011 corresponds to the connected part, e.g., between a ball or bump and an electrode of the first face 421a of the BGA, and the second connected part 5012 corresponds to the connected part between the ball or bump and an electrode of the second face 421b.

Figure 15:
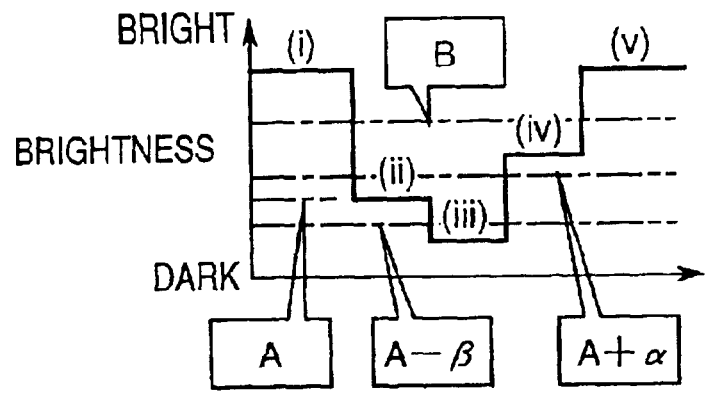
FIG. 15 is a graph obtained by converting the transmission image of FIG. 14 to brightness information.

FIG. 15 is a graph obtained by, e.g., plotting a brightness on a chain line 5014 of the transmission image 501. Labels (i)–(v) in FIG. 15 correspond to parts (i)–(v) of FIG. 14, respectively, showing brightness levels thereof. Parts (i) and (v) are brightest, that is, closer to white, whereas the part (iii) is darkest, i.e., closer to black. The transmission image 501 is binarized by the brightness value of a level B which is lower than the level of the parts (i) and (v) as background parts of the transmission image 501 and exceeding the level of the part (iv) as is clear from FIG. 15, and consequently, an image of only the extracted first connected part 5011 and second connected part 5012 including the overlapping part 5013 is obtained as designated by a reference numeral 502 in FIG. 16.

In step 105, the image forming device 451 binarizes the obtained transmission image by a binarization level by which both the first connected part and the second connected part can be displayed, thereby producing a binary image.

In step 106, the image forming device 451 binarizes the transmission image 501 by a bright side level (A+$\alpha$) which is lower than the brightness level of the second connected part 5012, specifically, lower than the brightness level of the part (iv), and exceeds the average brightness level A corresponding to the brightness level of the first connected part 5011. This binarization forms an image of only the extracted first connected part 5011 including the overlapping part 5013 as indicated by a reference numeral 503 in FIG. 16.

In step 107, the image forming device 451 binarizes the transmission image 501 by a dark side level (A−$\beta$) which is lower than the average brightness level A as the brightness level of the first connected part 5011 and exceeds the brightness level of the overlapping part 5013, i.e., exceeds the brightness level of the part (iii). The binarization generates an image of only the extracted overlapping part 5013 as designated by a reference numeral 504 in FIG. 16.

The above values $\alpha$ and $\beta$ as addition and subtraction command values to the average brightness level A are set not to include brightnesses of the first connected part 5011 and second connected part 5012 with reference to the brightnesses of the first connected part 5011 and second connected part 5012 when the average brightness level A is obtained.

Figure 16:
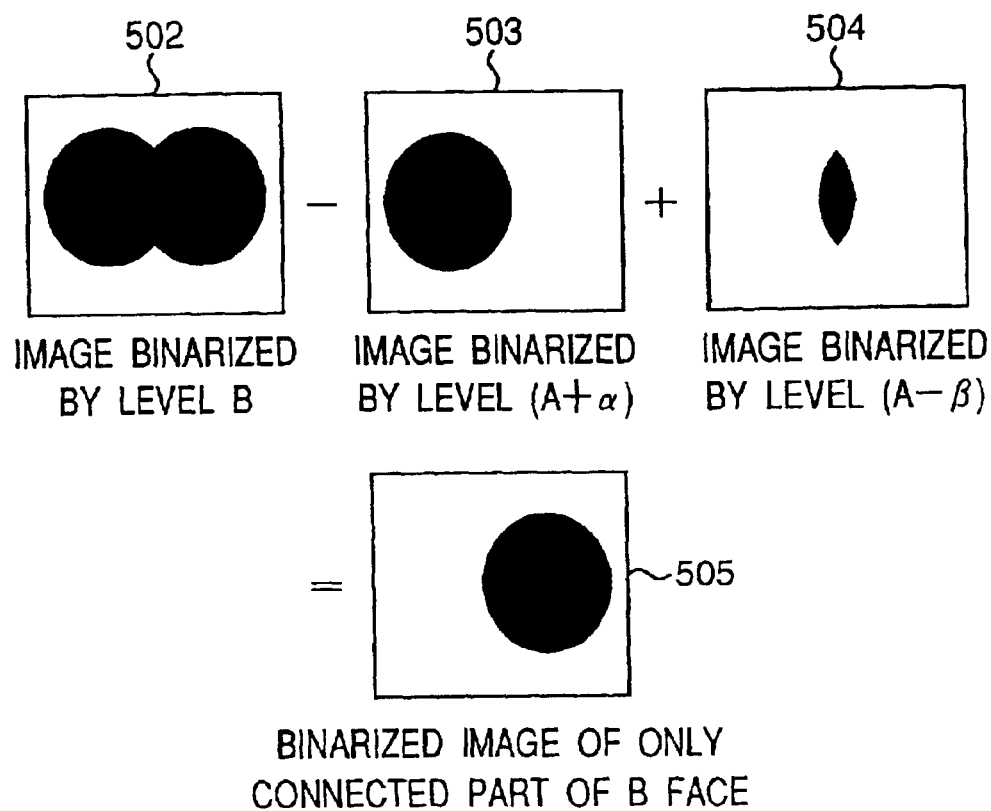
FIG. 16 is a diagram explanatory of a connection inspecting method in the third embodiment carried out by the connection inspecting apparatus of FIG. 13.

In step 108, the image forming device 451 synthesizes the above three images 502, 503 and 504. More specifically, as indicated in FIG. 16, the image 503 of only the first connected part 5011 including the overlapping part 5013 is deleted from the image 502 of the first connected part 5011 and second connected part 5012 including the overlapping part 5013, to which the image 504 of only the overlapping part 5013 is added, whereby an image 505 of only the second connected part 5012 including the overlapping part 5013 is obtained.

Although the above description is related to one set of the first connected part 5011 and second connected part 5012, the same process is carried out to all connected parts of the transmission images obtained in step 104. However, in a case, e.g., where all connected parts are apparently in the equal connection state, the inspection may be representatively executed only to one set of the first connected part 5011 and second connected part 5012, with the inspection to the other parts being omitted.

In step 109, the image forming device 451 inspects, based on the image 505, a shape and a connection position of the second connected part 5012. After the inspection, the control device 481 stops the application of X-rays from the irradiation device 411 in step 110. Whether the production is to be finished or not is judged in step 111. The inspection process is terminated when the production is to be finished. The process returns to step 102 if there are boards yet to be inspected.

Since the image forming device 451 can obtain the image of only the connected part of the electronic component mounted later, that is, the image of only the second connected part 5012 in the above example from the transmission image of the so-called double face-mounted board, whether the shape and connection position of the second connected part 5012 are good or not, that is, whether the connection position and connection shape of, e.g., an electrode part on the second face 421$b$ and an electrode of the electronic component 422 are good or not can be judged on the basis of the obtained image of only the second connected part 5012. The connection shape referred to above corresponds to a shape of, e.g., the solder ball connecting the electrode part on the second face 421$b$ and the electrode of the electronic component 422.

In the arrangement according to the third embodiment as above in comparison with the related art, a quantity of data to be stored can be reduced. Moreover, finally, since the image of the second connected part 5012 is formed on the basis of the image picked up in a state with the electronic components 422 mounted to both the first face 421$a$ and the second face 421$b$, conventional troublesome operations of registering the picked image in a state with the electronic component 422 mounted only to the first face 421$a$ and the picked image in a state with the electronic components 422 mounted to the first face 421$a$ and second face 421$b$, managing IDs for making sure identity between the board with the electronic component 422 mounted to one face 421$a$, and the board with the electronic components 422 mounted to both the first face 421$a$ and the second face 421$b$, etc. can be eliminated.

Without the need for the registration, a perfect image of only the second connected part 5012 can be obtained even when the board deflects during soldering with the use of a reflow or the like.

Fourth Embodiment

As is made clear from the above description of the connection inspecting method in the third embodiment, binary images of the first connected part 5011 and second connected part 5012 are obtained by the levels (A+α) and (A−β) with reference to the average brightness level A, respectively. Therefore, the method is effective for the case where the first connected part 5011 and second connected part 5012 are different in brightness in the transmission image. Specifically, when the electrode part on the board and the electrode of the electronic component are connected by the solder balls, respectively, the difference of brightness corresponds to a case where, for instance, the solder ball of the first face 421$a$ and the solder ball of second face 421$b$ are different, e.g., in thickness.

On the other hand, a connection inspecting method according to a fourth embodiment is applicable even to a case where the first connected part 5011 and second connected part 5012 are equal in brightness.

Figure 18:
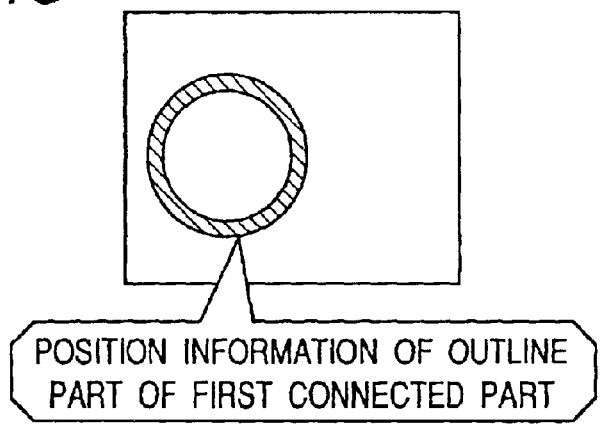
FIG. 18 is a diagram explanatory of a connection inspecting method in a fourth embodiment carried out by the connection inspecting apparatus of FIG. 13, which shows an outline position.
Figure 22:
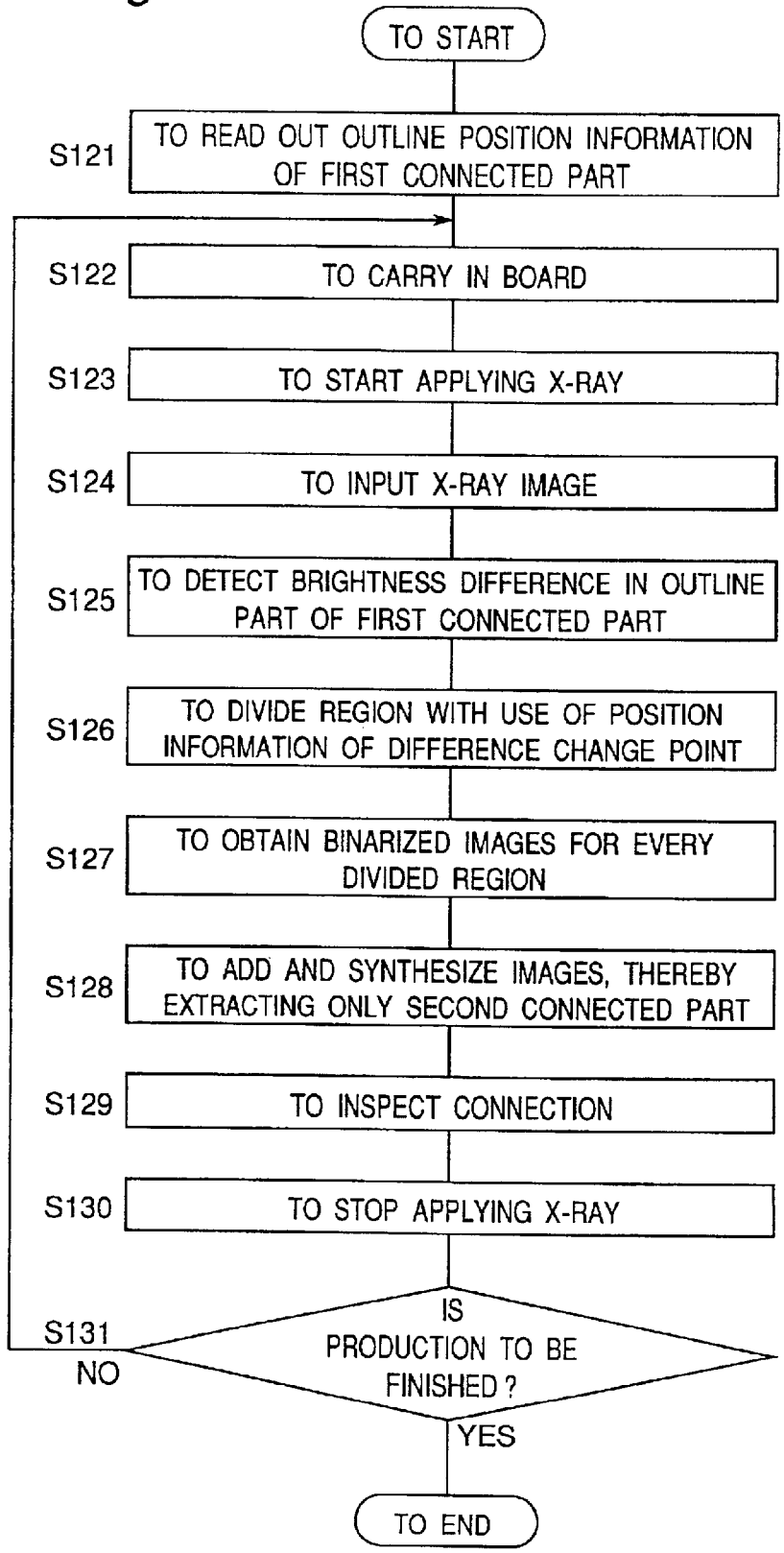
FIG. 22 is a flow chart of the connection inspecting method in the fourth embodiment carried out by the connection inspecting apparatus of FIG. 13.

In step 121 of FIG. 22, based on the X-ray image of the first connected part obtained through the X-ray pickup in a state with the electronic component 422 mounted only to the first face 421$a$, the image forming device 451 stores position information of an outline part of the first connected part 5011 as ring-shaped data into the memory 4512 as shown in FIG. 18. A breadth, namely, an allowance for a position of the outline as illustrated is to absorb effects of a displacement by shrinkage of the board 421. Position information of each first connected part 5011 on the first face 421$a$ can be obtained from design data of the board 421 and the above positional allowance. At the same time, a quantity of relative displacement between the electrode part of the board 421 and the electrode of the electronic component is determined on the design because the connected part to be inspected in the fourth embodiment is a connected part between the electrode part of the board 421 and the electrode of the electronic component. Accordingly, a size of the above allowance for the outline; position can be determined on the basis of the quantity of relative displacement. About ⅓ of a breadth of an electrode of the electrode part on the board 421 is determined as the allowance in this example. The breadth of the electrode corresponds to each diameter of the first connected part 5011 and second connected part 5012 in the fourth embodiment.

Steps 122–124 are carried out thereafter, whereby the transmission image of the so-called double face-mounted board is supplied to the image forming device 451. The steps 122–124 correspond to the steps 102–104, the detailed description of which will be omitted here.

Figure 19:
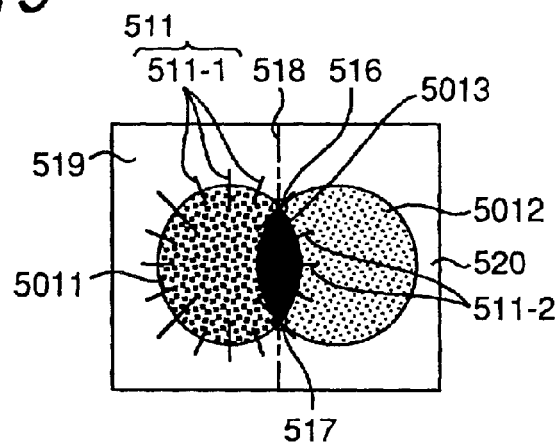
FIG. 19 is a diagram explanatory of the connection inspecting method in the fourth embodiment carried out by the connection inspecting apparatus of FIG. 13, which shows a divide line.
Figure 20:
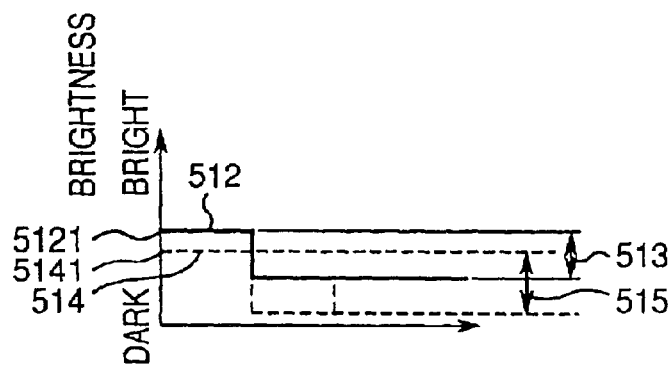
FIG. 20 is a diagram explanatory of the connection inspecting method in the fourth embodiment carried out by the connection inspecting apparatus of FIG. 13 to explain a brightness change of an outline part.

In step 125, as shown in FIG. 19, the image forming device 451 obtains a change in brightness for every detect position 511 radially disposed from the center of the first connected part 5011 in a range of the position information of the outline in the X-ray image of the board with the electronic components 422 mounted to both the first face 421$a$ and the second face 421$b$. The brightness change information obtained in this manner varies depending on whether the detect position includes the overlapping part 5013 or not as is clear from FIG. 19. In other words, for example, the brightness change at a detect position 511-1 not including the overlapping part 5013 is such as indicated by a solid line of a reference numeral 512 of FIG. 20, and a brightness difference between the outline position and a position outside the outline is of a level indicated by a reference numeral 513. Meanwhile, the brightness change at a detect position 511-2 including the overlapping part 5013 is as indicated by a chain line of a reference numeral 514 of FIG. 20 and a brightness difference between the outline position and the position outside the outline becomes a level 515 larger than the above level 513. A quantity of the brightness change differs whether or not the detect position includes the overlapping part 5013. Moreover, the brightness level at a detection start point becomes different as is understood from a brightness 5121 at the detection start point of the detect position 511-1 and a brightness 5141 at the detection start point of the detect position 511-2.

The image forming device 451 obtains on the basis of the position information of the outline, a position of a part where the brightness change starts to differ from the other parts. The obtained position is a position where the first connected part 5011 and second connected part 5012 start intersecting, that is, opposite end positions of the overlapping part 5013, namely, one position 516 and the other position 517.

Preferably, the detect positions 511 are first set relatively roughly, and change points are roughly searched by detecting the level change, and the brightness change of the detection start points. Then, detect positions 511 are set finely in the vicinity of the roughly obtained change points. The one position 516 and the other position 517 as correct change points are searched for in this way.

In step 126, the image forming device 451 obtains a divide line 518 passing the two positions, one position 516 and the other position 517 based on the position information of the points obtained in step 125. The transmission image 501 in FIG. 14 is divided by the divide line 518 to a first region 519 including the first connected part and a second region 520 including the second connected part.

Figure 21:
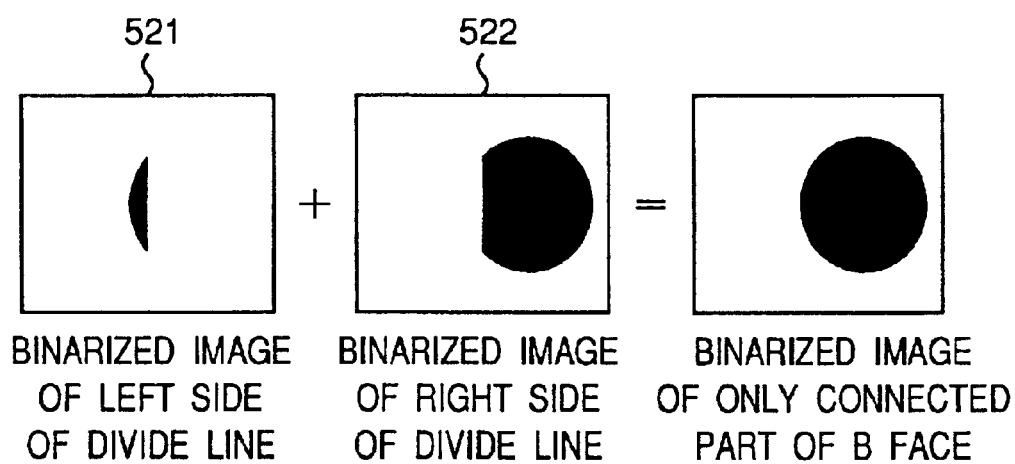
FIG. 21 is a diagram explanatory of the connection inspecting method in the fourth embodiment carried out by the connection inspecting apparatus of FIG. 13.

In step 127, the image forming device 451 binarizes the transmission image 501 at the first region 519 by the level (A−β), whereby a binary image as designated by a reference numeral 521 in FIG. 21 which corresponds to a left half of the overlapping part 5013 is obtained. Further, the image forming device 451 binarizes the transmission image 501 at the second region 520 by the level (A+α), or deletes an image at the first region 519 from the transmission image 501, whereby a binary image as indicated by a reference numeral 522 in FIG. 21 which is formed by deleting the left half of the overlapping part 5013 from the binary image of the second connected part 5012 is obtained.

In step 128, the image forming device 451 adds these images 521 and 522, thereby obtaining the image 505 of only the second connected part 5012 including the overlapping part 5013.

Succeeding steps 129–131 correspond to the earlier described steps 109–111, and the description thereof will be omitted here.

According to the connection inspecting method of the fourth embodiment as discussed above, not only is the effect in the connection inspecting method of the third embodiment exhibited, but the image of only the second connected part 5012 can be obtained from the transmission image 501 of the so-called double face-mounted board even when the first connected part 5011 and second connected part 5012 are hardly different in brightness or are equal in brightness. Concretely, even when the solder balls are nearly equal or equal in thickness in all electronic components 422.

In the above description on the connection inspecting method of the fourth embodiment, position information of the outline is obtained on the basis of the transmission image in a state of the so-called one-sided mounting with the electronic component mounted 422 only to the first face 421a. However, the information is not obtained specifically in this method, that is, may be calculated from the position information and quantity of allowable displacement on the design of the first connected part 5011 to be inspected.

Fifth Embodiment

In order to obtain the one position 516 and the other position 517 necessary for obtaining the divide line 518 in the above-described connection inspecting method of the fourth embodiment, the brightness change of each one of the radially arranged detect positions 511 is obtained for the outline position of the first connected part 5011.

A connection inspecting method according to a fifth embodiment is an improvement of the above method of the fourth embodiment. The brightness level of the transmission image 501 is extremely low at the one position 516 and the other position 517 as is clear from the foregoing description with reference to FIG. 20. According to the connection inspecting method of the fifth embodiment, the brightness level at the transmission image 501 is obtained for the plurality of detect positions 511 in step 145 of FIG. 23, from which a start position showing a lower limit peak of the brightness level is detected. The above one position 516 and the other position 517 are eventually obtained accordingly. In step 146, the divide line 518 is obtained on the basis of the one position 516 and the other position 517 obtained in step 145.

The other steps 141–144 and steps 147–151 are operations equal to steps 121–124 and steps 127–131 described with reference to FIG. 22, the description of which will be omitted here.

According to the connection inspecting method of the fifth embodiment, the effect by the foregoing connection inspecting method of the fourth embodiment is exerted, and moreover, an inspection process time can be shortened in comparison with the connection inspecting method of the fourth embodiment. Since detect values of the brightness at the outline position detected by the connection inspecting methods of the fourth and fifth embodiments actually include variations, the detect values should be averaged or processed in the like manner to obtain the brightness levels 513 and 515, or brightnesses 5121 and 5141 at the detection start points in the connection inspecting method of the fourth embodiment. To the contrary, to simply detect the lower limit peak is enough in the connection inspecting method of the fifth embodiment, and the lower limit peak is extremely different in brightness level from the other parts, thereby eliminating the need of averaging the detect values of the brightness or the like process. The inspection process time can hence be shortened as compared with the connection inspecting method of the fourth embodiment.

Sixth Embodiment

According to a sixth embodiment of the connection inspecting method, in the connection inspecting methods of the above third-fifth embodiments, an image storage time when the so-called double face-mounted board is picked up is changed. More specifically, in a case of, for example, two points to be inspected which are greatly different in thickness, it happens that the transmission image cannot be obtained for a thick part because of a considerably small quantity of X-rays passing under the first X-ray application condition in which the transmission image can be obtained for a thin part. On the other hand, the quantity of X-rays passing the thin part becomes excessive and saturated under the second X-ray application condition in which the transmission image can be obtained for the thick part.

Appropriate transmission images are obtained for both the thin and the thick parts by changing a time for picking up the transmission image, in other words, an image storage time in the connection inspecting method of the sixth embodiment. The method adopts a technique enabling connection inspection even to the parts of extremely different thicknesses to be inspected as above by synthesizing the appropriate transmission images.

Figure 17:
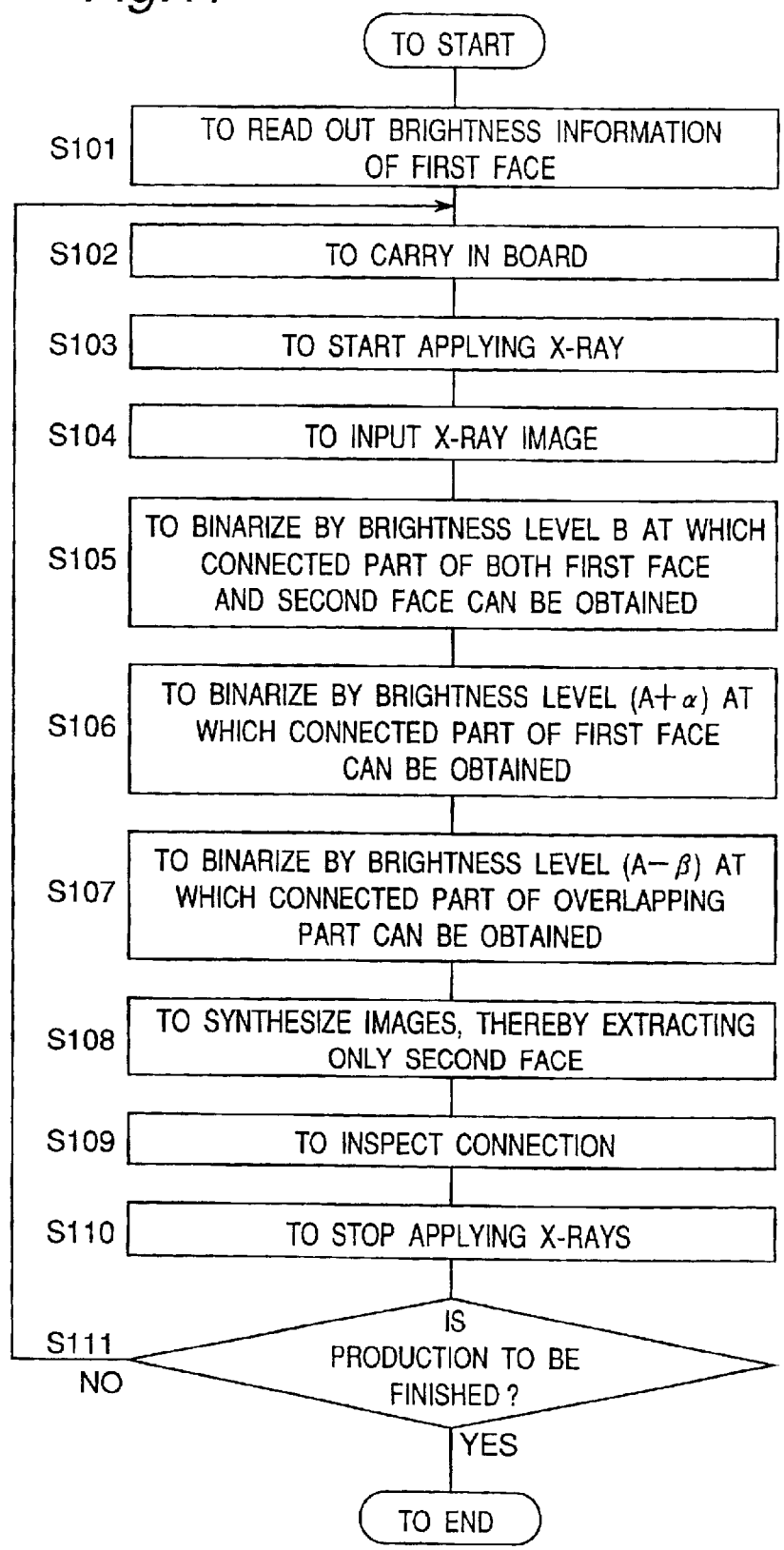
FIG. 17 is a flow chart of the connection inspecting method in the third embodiment carried out by the connection inspecting apparatus of FIG. 13.
Figure 24:
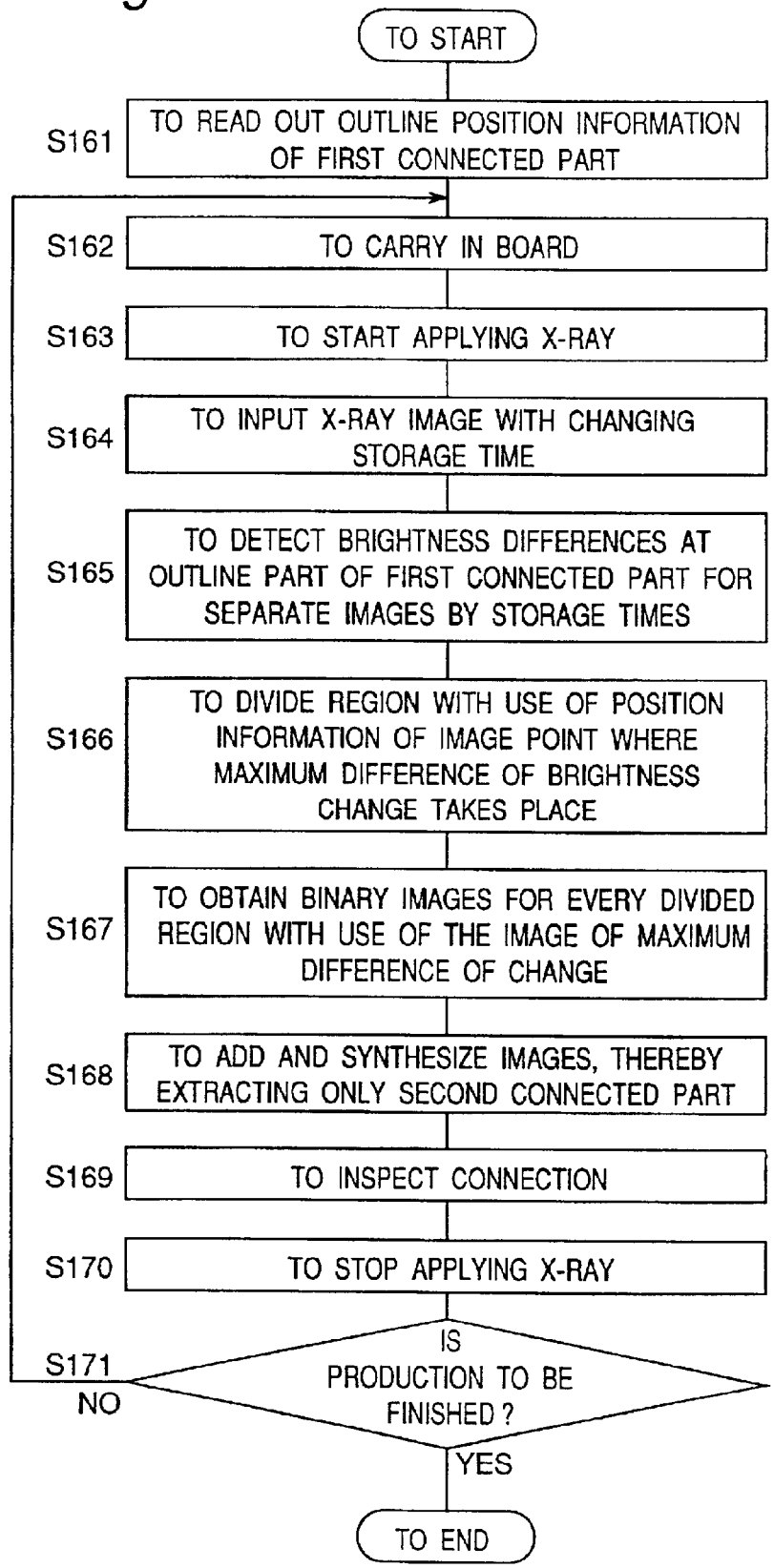
FIG. 24 is a flow chart of a connection inspecting method in a sixth embodiment carried out by the connection inspecting apparatus of FIG. 13.

For instance, steps 161–171 of the connection inspecting method shown in FIG. 24 correspond to steps 101–111 in the connection inspecting method of the third embodiment discussed with reference to FIG. 17 and steps 121–131 in the connection inspecting method of the fourth embodiment described with reference to FIG. 22. Steps 161–163 are operations equal to steps 101–103 and 121–123. These steps will be omitted from the description herein.

The transmission image is obtained by changing the storage time to the double face-mounted board, for example, in step 164 corresponding to step 124 in the connection inspecting method of the fourth embodiment. The brightness difference of the outline part of the first connected part 5011 is detected for each of images corresponding to the storage times in step 165 corresponding to step 125. The transmission image of the storage time having a largest brightness difference among the brightness differences obtained in step 165 is divided with use of the position information of the one position 516 and the other position 517 instep 166 corresponding to step 126. Succeeding steps 167–171 are equal to steps 107–111 and 127–131, and will not be described here.

Figure 23:
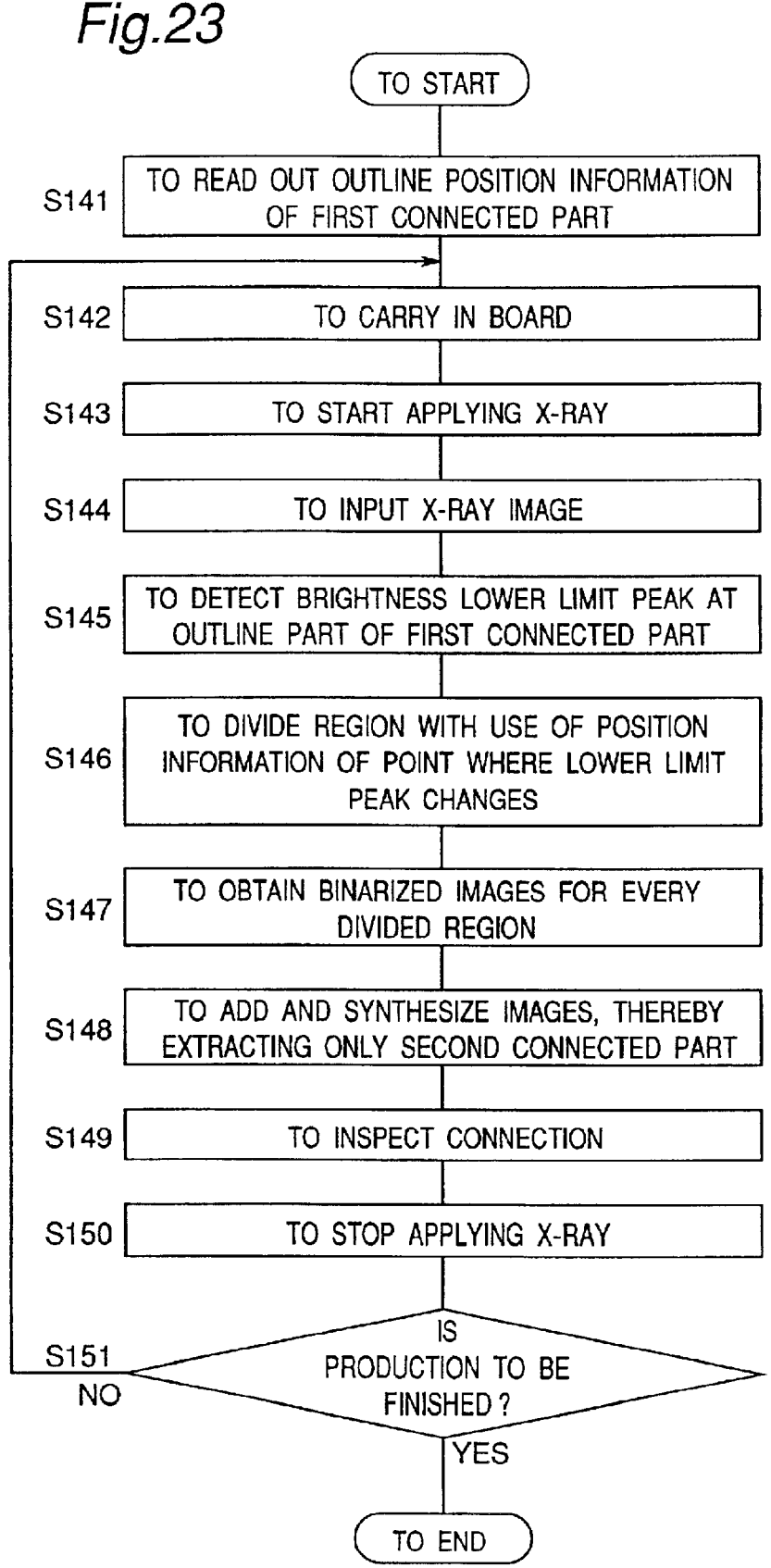
FIG. 23 is a flow chart of a connection inspecting method in a fifth embodiment carried out by the connection inspecting apparatus of FIG. 13.
Figure 25:
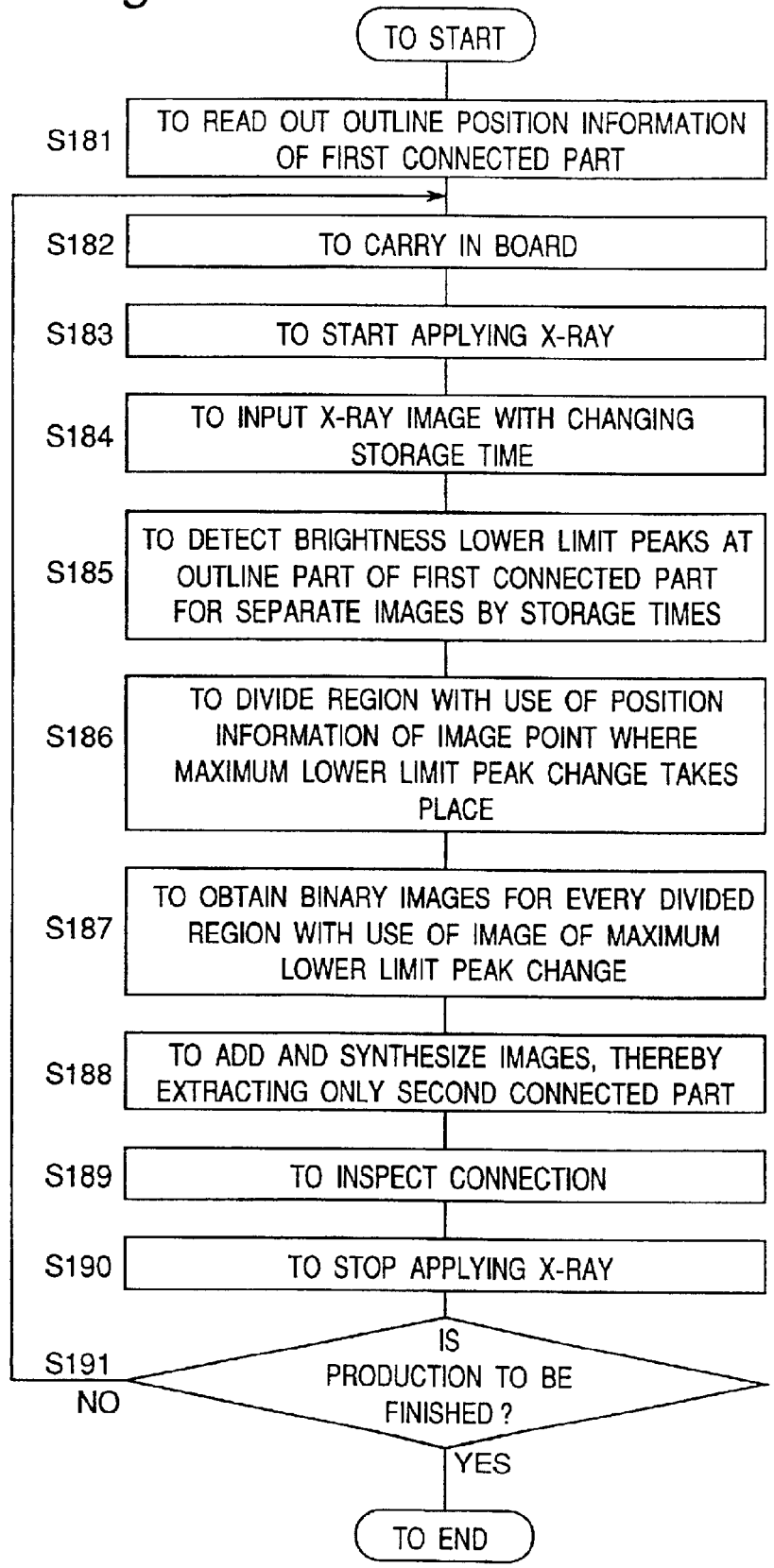
FIG. 25 is a flow chart of the connection inspecting method in the sixth embodiment carried out by the connection inspecting apparatus of FIG. 13.

Steps 181–191 of the connection inspecting method shown in FIG. 25 correspond respectively to steps 141–151 in the connection inspecting method of the third embodiment described with reference to FIG. 23, and steps 181–183 are equal operations to steps 141–143, the description of which will therefore be omitted here.

The transmission image is obtained by picking up the double face-mounted board with changing the storage time in step 184 corresponding to step 144 in the connection inspecting method of the fifth embodiment. In step 185 corresponding to step 145, the lower limit peak of the brightness of the outline part of the first connected part 5011 is detected for each of images by the storage times. In step 186 corresponding to step 146, the transmission image of the storage time having the lower peak including a minimum brightness level among the lower limit peaks obtained in step 185 is divided with the use of position information of the one position 516 and the other position 517. Since the following steps 187–191 are equal operations to steps 147–151, the description will be omitted.

The connection inspecting method according to the sixth embodiment as above not only carries the effects obtained by the connection inspecting methods of the third through fifth embodiments, but ensures a reliability on connection inspection even when the connected part changes its thickness on the board to be inspected.

Figure 26:
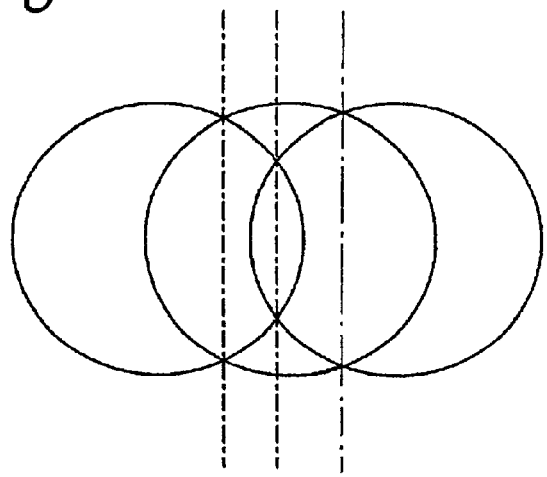
FIG. 26 is a diagram for explaining that the present invention is applicable also to the case where electronic components are mounted in three or more layers.

Although the electronic components are set to the first face 421a and second face 421b at most in each of the above embodiments, the present invention is applicable further to a case where electronic components are present in each of three or more layers. For example, when the electronic components are present in three respective layers, as shown in FIG. 26, three divide lines at overlapping parts of connected parts which correspond to the divide line 518 are formed at a maximum. The binarization level is obtained for each region and a naturally desired image is obtained on the basis of resulting binary images, similar to each of the above third-fifth embodiments.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A connection inspecting apparatus for inspecting connection of a connected part, said connection inspecting apparatus comprising:

an irradiation part for applying radiation to the connected part of members with an application condition being invariant;

a scintillator for converting the radiation passed through the connected part to a visible light;

an imaging device for picking up a plurality of transmission images of the connected part generated from said scintillator for a plurality of different storage times;

a sub-thickness image forming device for forming a plurality of sub-thickness images corresponding respectively to the plurality of transmission images of the plurality of different storage times supplied from said imaging device based on a relationship between a brightness density of the plurality of transmission images and a thickness of the connected part; and a superimposed image forming device for forming a thickness superimposed image of the connected part by adding the plurality of the sub-thickness images to each other, wherein said superimposed image forming device forms the thickness superimposed image of the connected part by adding the plurality of sub-thickness images to each other when a value of the thickness of the connected part is within a certain range, and extracts and collects only valid parts of the plurality of sub-thickness images, respectively, so as to form the thickness superimposed image when the value of the thickness of the connected part is not within the certain range.

2. The connection inspecting apparatus according to claim 1, wherein said sub-thickness image forming device forms a plurality of first sub-thickness images corresponding to the respective plurality of transmission images at the plurality of different storage times when one connected part is present along an application direction of the radiation, and forms a plurality of second sub-thickness images corresponding to each of the plurality of transmission images at the plurality of different storage times in a state with connected parts overlapping when a plurality of connected parts are present overlapping in the application direction of the radiation, and said superimposed image forming device forms a first superimposed image by adding the plurality of first sub-thickness images to each other and also forms a second superimposed image by adding the plurality of second sub-thickness images to each other, and subtracts the first superimposed image from the second superimposed image so as to form the thickness superimposed image.

3. The connection inspecting apparatus according to claim 2, wherein when the connected parts are present at opposite faces of a plate-shaped member, the first superimposed image formed by said sub-thickness image forming device corresponds to the connected part at a first face of the opposite faces, and the second superimposed image corresponds to the connected parts at both of the opposite faces, so that said superimposed image forming device obtains the thickness superimposed image of the connected part at a second face of the opposite faces by subtracting the first superimposed image from the second superimposed image.

4. The connection inspecting apparatus according to claim 2, wherein said superimposed image forming device extracts and collects only valid parts from the plurality of first sub-thickness images, respectively, so as to form the first superimposed image, and extracts and collects only valid parts from the plurality of second sub-thickness images so as to form the second superimposed image.

5. The connection inspecting apparatus according to claim 1, further comprising a teaching jig of a known thickness for obtaining the relationship between the brightness density of the plurality of transmission images and the thickness of the connected part, said teaching jig being formed of a material with a radiation transmittance equal to that of the connected part.

6. A connection inspecting method for inspecting a connected part, said connection inspecting method comprising:

applying radiation to the connected part of members with an application condition being invariant, and then converting the radiation passed through the connected part to visible light;

picking up a plurality of transmission images of the connected part expressed by the visible light for a plurality of different storage times;

forming a plurality of images corresponding respectively to the plurality of transmission images of the plurality of different storage times based on a relationship between a brightness density of the plurality of transmission images and a thickness of the connected part; and forming a thickness superimposed image by adding the plurality of sub-thickness images to each other so as to inspect the connected part when a value of the thickness of the connected part is within a certain range, and forming the thickness superimposed image by extracting and collecting only valid parts of the plurality of sub-thickness images, respectively, when the value of the thickness of the connected part is not within the certain range.

7. The connection inspecting method according to claim 6, wherein, when a plurality of connected parts are present overlapping in an application direction of the radiation, said forming of the plurality of sub-thickness images comprises:

forming a plurality of first sub-thickness images at the plurality of different storage times in a state where one connected part is present along the application direction of the radiation; and forming a plurality of second sub-thickness images at the plurality of different storage times in a state where the plurality of connected parts are present overlapping in the application direction of the radiation, and said forming of the thickness superimposed image comprises:

forming a first thickness superimposed image by adding the plurality of first sub-thickness images to each other, and forming a second thickness superimposed image by adding the plurality of second sub-thickness images to each other; and subtracting the first thickness superimposed image from the second thickness superimposed image.

8. The connection inspecting method according to claim 7, wherein said forming of the first thickness superimposed image comprises extracting and collecting only valid parts from the plurality of first sub-thickness images, respectively, and said forming of the second thickness superimposed image comprises extracting and collecting only valid parts from the plurality of the second sub-thickness images.

9. A program on a computer readable recording medium to make a computer execute, said program comprising:

a process for applying radiation to a connected part of members with an application condition being invariant, and converting the radiation passed through the connected part to a visible light;

a process for picking up a plurality of transmission images of the connected part expressed by the visible light for a plurality of different storage times;

a process for forming sub-thickness images corresponding respectively to the plurality of transmission images of the plurality of different storage times based on a relationship between a brightness density of the plurality of transmission images and a thickness of the connected part; and a process for adding the plurality of sub-thickness images to each other so as to form a thickness superimposed image when a value of the thickness of the connected part is within a certain range, and extracting and collecting only valid parts of the plurality of sub-thickness images, respectively, so as to form the thickness superimposed image when the value of the thickness of the connected part is not within the certain range.

10. The program according to claim 9, wherein when connected parts are present at opposite faces of a plate-shaped member, said process of forming the sub-thickness image forms a plurality of first sub-thickness images corresponding to the plurality of transmission images at the plurality of storage times for the connected part present at a first face of the opposite faces, and forms a plurality of second sub-thickness images corresponding to the plurality of transmission images at the plurality of different storage times in a state where the connected parts are present overlapping at the opposite faces in an application direction of the radiation, and said process of forming the thickness superimposed image forms a first thickness superimposed image by adding the plurality of first sub-thickness images to each other, forms a second thickness superimposed image by adding the plurality of second sub-thickness images to each other, and subtracts the first thickness superimposed image from the second thickness superimposed image so as to form the thickness superimposed image of the connected part present at a second face of the opposite faces.

11. A connection inspecting apparatus comprising:

an irradiation device for applying radiation to an object to be inspected having a first connection part and a second connection part;

a scintillator for converting the radiation passed through the object to visible light;

an imaging device for picking up a transmission image of the object generated from said scintillator; and an image forming device for forming brightness information based on the transmission image supplied from said imaging device of the first connected part and the second connected part of the object to be inspected which overlap at an overlapping part in a thicknesswise direction thereof, and for forming an image of only the second connected part based on the brightness information.

12. The connection inspecting apparatus according to claim 11, wherein said image forming device binarizes the brightness information so as to form the image of only the second connected part by a bright side level ($A+\alpha$) brighter than a reference brightness level ($A$) of a transmission image of the first connected part when the object has only the first connected part and by a dark side level (A−β) darker than the reference brightness level.

13. The connection inspecting apparatus according to claim 12, wherein, based on an image of the first connected part and the second connected part overlapping obtained by binarizing the brightness information, an image of only the first connected part obtained by the binarization by the bright side level, and an image of the overlapping part obtained by the binarization by the dark side level, said image forming device deletes the image of only the first connected part from the image of the first and second connected parts, and adds the image of the overlapping part thereto so as to form the image of only the second connected part.

14. The connection inspecting apparatus according to claim 11, wherein said image forming device obtains outline position information of the first connected part based on the transmission image of the first connected part, and forms the image of only the second connected part based on the brightness information and the outline position information.

15. The connection inspecting apparatus according to claim 14, wherein said image forming device detects a brightness change at an outline position indicated by the outline position information by using the brightness information, obtains position information of a first position and a second position in an outline segment of the overlapping part showing a different brightness change from other positions, obtains information on a divide line passing the first position and the second position from the position information, and forms the image of only the second connected part from the brightness information by changing a binarization level at a first region including the first connected part and a second region including the second connected part which are divided by the divide line.

16. The connection inspecting apparatus according to claim 15, wherein the binarization level formed by said image forming device at the divided first region including the first connected part is a level for extracting only the overlapping part, while the binarization level at the second region including the second connected part is a brightness level of the second connected part obtained when the position information of the first position and the second position is obtained.

17. The connection inspecting apparatus according to claim 15, wherein said image forming device obtains the position information of the first position and the second position based on a peak value of brightness.

18. The connection inspecting apparatus according to claim 15, wherein said imaging device picks up an image of the first connected part and the second connected part in an overlap state with a plurality of different image storage times, and said image forming device obtains the first position and the second position in the outline segment of the overlapping part by using the brightness information of a largest brightness change among the brightness information of transmission images for every one of the plurality of different image storage times.

19. The connection inspecting apparatus according to claim 18, wherein said image forming device obtains the position information of the first position and the second position based on the brightness information of a largest peak value of brightness.

20. The connection inspecting apparatus according to claim 11, wherein said imaging device picks up an image of the first connected part and the second connected part in an overlap state with a plurality of image storage times.

21. A connection inspecting method comprising:

applying a radiation to an object to be inspected which has a first connected part overlapping with a second connected part at an overlapping part in a thicknesswise direction of the object, and converting a the radiation passed through the object to visible light;

forming brightness information based on a transmission image of the first connected part and the second connected part in an overlap state which is obtained through the converting to the visible light; and forming an image of only the second connected part based on the brightness information.

22. The connection inspecting method according to claim 21, wherein said forming of the image of only the second connected part comprises:

binarizing the brightness information so as to obtain an image of the first connected part and the second connected part in the overlap state;

binarizing the brightness information by a bright side level (A+α) brighter than a reference brightness level (A) at a transmission image of the first connected part when the object has only the first connected part so as to obtain an image of only the first connected part;

binarizing the brightness information by a dark side level (A−β) darker than the reference brightness level so as to obtain an image of the overlapping part; and deleting the image of only the first connected part from the image of the first connected part and the second connected part, and adding the image of the overlapping part thereto, whereby the image of only the second connected part is formed.

23. The connection inspecting method according to claim 21, wherein said forming of the image of only the second connected part comprises:

obtaining outline position information of the first connected part based on a transmission image of the first connected part by using the brightness information;

detecting a brightness change at an outline position indicated by the outline position information;

obtaining position information of a first position and a second position in an outline segment of the overlapping part showing a different brightness change from other positions;

obtaining information on a divide line passing the first position and second position from the position information; and binarizing for a first region including the first connected part divided by the divide line by a level in which only the overlapping part is extracted, and binarizing for a second region including the second connected part by a brightness level of the second connected part obtained when the position information of the first position and second position are obtained, so that the image of only the second connected part is formed from the brightness information.

24. The connection inspecting method according to claim 23, wherein the position information of the first position and second position are obtained based on a peak value of brightness.

25. The connection inspecting method according to claim 21, wherein the first connected part and the second connected part in the overlap state are picked up by a plurality of different image storage times.

26. A program on a computer readable recording medium to make a computer execute, said program comprising:

a process of applying a radiation to an object to be inspected which has a first connected part overlapping with a second connected part at an overlapping part in a thickness direction of the object;

a process of forming brightness information based on a transmission image of the first connected part and the second connected part in an overlap state which is obtained by converting the radiation passed through the object to visible light; and a process of forming an image of only the second connected part based on the brightness information.

27. The program according to claim 26, wherein said process of forming the image binarizes the brightness information so as to obtain an image of the first connected part and the second connected part in the overlap state, binarizes the brightness information by a bright side level (A+α) brighter than a reference brightness level (A) at a transmission image of the first connected part when the object has only the first connected part so as to obtain an image of only the first connected part, binarizes the brightness information by a dark side level (A+α) darker than the reference brightness level so as to obtain an image of the overlapping part, and deletes the image of only the first connected part from the image of the first connected part and second connected part, and adds the image of the overlapping part thereto so as to form the image of only the second connected part.

28. The program according to claim 26, wherein said process of forming the image of only the second connected part obtains outline position information of the first connected part based on the transmission image of the first connected part with the use of the brightness information, detects a brightness change in an outline position indicated by the outline position information, obtains position information of a first position and a second position in an outline segment of the overlapping part showing a different brightness change from other positions, obtains information on a divide line passing the first position and the second position from the position information, binarizes a first region including the first connected part divided by the divide line by a level in which only the overlapping part is extracted, and binarizes a second region including the second connected part by a brightness level of the second connected part obtained when the position information of the first position and the second position are obtained, so that the image of only the second connected part is formed from the brightness information.

29. The program according to claim 26, wherein said process of forming the image of only the second connected part obtains outline position information of the first connected part based on an image of the first connected part by using the brightness information, detects a brightness peak value in an outline position indicated by the outline position information, obtains position information of a first position and a second position of an outline segment of the overlapping part by setting detected peaks as the first position and the second position, obtains information on a divide line passing the first position and the second position from the position information, binarizes a first region including the first connected part divided by the divide line by a level in which only the overlapping part is extracted, and binarizes a second region including the second connected part by a brightness level of the second connected part obtained when the position information of the first position and the second position are obtained, so that the image of only the second connected part is formed from the brightness information.

30. The program to claim 26, wherein the brightness information is formed based on the transmission image of the first connected part and the second connected part in the overlap state by picking up the image of the first connected part and second connected part with a plurality of different image storage times.

* * * * *

UNITED STATES PATENT AND TRADEMARK OFFICE
CERTIFICATE OF CORRECTION

PATENT NO. : 6,872,949 B2
DATED : March 29, 2005
INVENTOR(S) : Seiji Mizuoka et al.

It is certified that error appears in the above-identified patent and that said Letters Patent is hereby corrected as shown below:

Column 29,
Line 21, please replace "$(A+\alpha)$" with -- $(A+\beta)$ --.

Signed and Sealed this

Seventh Day of June, 2005

JON W. DUDAS
*Director of the United States Patent and Trademark Office*